(12) United States Patent
Bertino et al.

(10) Patent No.: US 7,576,188 B2
(45) Date of Patent: Aug. 18, 2009

(54) ANTITUMORAL TREATMENTS

(75) Inventors: Joseph R. Bertino, New Brunswick, NJ (US); Debabrata Barnejee, New Brunswick, NJ (US); Saydam Guray, New Brunswick, NJ (US); José Jimeno, Madrid (ES); Glynn Thomas Faircloth, Cambridge, MA (US)

(73) Assignee: Pharma Mar, S.A.U., Madrid (ES)

( * ) Notice: Subject to any disclaimer, the term of this patent is extended or adjusted under 35 U.S.C. 154(b) by 299 days.

(21) Appl. No.: 10/546,750

(22) PCT Filed: Mar. 12, 2004

(86) PCT No.: PCT/US2004/007606

§ 371 (c)(1),
(2), (4) Date: Nov. 4, 2005

(87) PCT Pub. No.: WO2004/080421

PCT Pub. Date: Sep. 23, 2004

(65) Prior Publication Data

US 2006/0178298 A1   Aug. 10, 2006

(51) Int. Cl.
*C07K 14/15* (2006.01)
*C12N 5/06* (2006.01)
*G01N 33/574* (2006.01)
*A61K 39/395* (2006.01)

(52) U.S. Cl. .................. 530/388.7; 435/343; 435/7.23; 424/138.1

(58) Field of Classification Search ........................ None
See application file for complete search history.

(56) References Cited

U.S. PATENT DOCUMENTS

| 4,493,796 | A |   | 1/1985  | Rinehart |
| 4,670,262 | A |   | 6/1987  | Battelli et al. |
| 4,952,399 | A |   | 8/1990  | Lewenstein et al. |
| 5,294,603 | A |   | 3/1994  | Rinehart |
| 5,462,726 | A |   | 10/1995 | Lodge |
| 5,580,871 | A |   | 12/1996 | Earl |
| 5,834,586 | A |   | 11/1998 | Rinehart et al. |
| 6,030,943 | A | * | 2/2000  | Crumb et al. ................... 514/9 |
| 6,034,058 | A |   | 3/2000  | Rinehart et al. |
| 6,153,731 | A |   | 11/2000 | Rinehart et al. |
| 6,156,724 | A |   | 12/2000 | Rinehart et al. |
| 6,245,759 | B1|   | 6/2001  | Bilodeau et al. |
| 6,710,029 | B1|   | 3/2004  | Rinehart et al. |
| RE39,887  | E |   | 10/2007 | Rinehart et al. |
| 2004/0010043 | A1 |   | 1/2004 | Lazaro et al. |
| 2005/0004012 | A1 |   | 1/2005 | Mangues et al. |
| 2006/0172926 | A1 |   | 8/2006 | Bertino et al. |

FOREIGN PATENT DOCUMENTS

| EP | 0048149 | 3/1982 |
| EP | 0393883 | 10/1990 |
| ES | 2102322 | 7/1997 |
| UA | 78188 | 3/2007 |
| WO | WO 91/04985 | 4/1991 |
| WO | WO 93/00362 | 1/1993 |
| WO | WO 98/17275 | 4/1998 |
| WO | WO 98/17302 | 4/1998 |
| WO | WO 99/42125 | 8/1999 |
| WO | WO 00/20411 A1 | 4/2000 |
| WO | WO-01/35974 | * 5/2001 |
| WO | WO 01/36974 | 5/2001 |
| WO | WO 01/76616 | 10/2001 |
| WO | WO 02/02596 | 1/2002 |
| WO | WO 02/30441 | 4/2002 |
| WO | WO 03/033013 | 4/2003 |
| WO | WO 2004/080421 | 9/2004 |

OTHER PUBLICATIONS da Rocha, 2001, Current Opinion in Pharmacology, 1, 364-369.*

Ady-Vago, N. et al., "L-Carnitine as a Protector Against Aplidine Induced Skeletal Muscle Toxicity," Proceedings of the American Association for Cancer Research, vol. 42, pp. 545 (Mar. 2001).

Bergeron, Raymond J. et al., "Antineoplastic and Antiherpetic Activity of Spermidine Catecholamide Iron Chelators," Biochemical and Biophysical Research Communications, vol. 121, No. 3, 848-854, 1984.

Chapa, AM. et al., "Influence of Intravenous L-Carnitine Administration In Sheep Preceding an Oral Urea Drench." Journal of Animal Science, vol. 76, No. 11, pp. 2930-2937, 1998.

Depenbrock, H. et al., "In vitro activity of aplidine, a new marine-derived anti-cancer compound, on freshly explanted clonogenic human tumour cells and haematopoietic-precursor cells," British Journal of Cancer, vol. 78, No. 6, 739-744, 1998.

Erba, E. et al., "Cell cycle phases perturbations induced by new natural marine compounds," Annals of Oncology ,vol. 7, Supplement 1, #283, pp. 82, 1996.

Faircloth, G. et al., "Aplidine (APL) is a novel marine-derived depsipeptide with in vivo antitumor activity," Proceedings of the American Association for Cancer Research. vol. 39, #1551, pp. 227, 1998.

Faircloth, G. et al., "Dehydrodidemnin B (DDB) a new marine derived anti-cancer agent (MDA) with activity against experimental tumor models" and Biological activity of thiocoraline. A new depsipeptide from a marine micromonospora,° Annals of Oncology. vol. 7, Supplement 1, #111 and #112, pp. 34, 1996.

Faircloth, G. et al., "Preclinical characterization of Aplidine (APD), a new marine anticancer depsipeptide (MADEP)," Proceedings of the American Association for Cancer Research, vol. 38, #692, pp. 103, 1997.

(Continued)

*Primary Examiner*—Andrew D Kosar
*Assistant Examiner*—Satyanarayana R Gudibande
(74) *Attorney, Agent, or Firm*—Kenneth H. Sonnenfeld; Michael A. Willis; King & Spalding LLP

(57) ABSTRACT

Aplidine and aplidine analogues are of use for the treatment of cancer, in particular in the treatment of leukemias and lymphomas, especially in combination therapies.

14 Claims, 15 Drawing Sheets

OTHER PUBLICATIONS

Faircloth, G. et al., "Preclinical development of aplidine, a novel marine-derived agent with potent antitumor activity," Annals of Oncology, vol. 9, Supplement 2, #129, pp. 34, 1998.

Faircloth, G. et al., Schedule-dependency of aplidine, a marine depsipeptide with antitumor activity, ° Proceedings of the American Association for Cancer Research, vol. 40, #2612, pp. 394-395, 1999.

Geldorf, Albert A. et al., "Cytotoxicity and neurocytotoxicity of new marine anticancer agents evaluated using in vitro assays," Cancer Chemother. Pharmacol. vol. 44, pp. 312-318, 1999.

Genin, Michael J. et al., "Synthesis and Crystal Structure of a Peptidomimetic Containing the (R)-4, 4-Spiro Lactam Type-II β-Turn Mimic," Journal of Organic Chemistry, vol. 58, No. 8, pp. 2334-2337, 1993.

Gomez-Fabre; P.M. et al., "Polamine contents of human breast cancer cells treated with the cytotoxic agents chlorpheniramine and dehydrodidemnin B," Cancer Letters, vol. 113, Nos. 1,2 pp. 141-144, 1997.

Goodman & Gilman's, The Pharacological Basis of Therapeutics, $9^{th}$ ed., Calabresi et al., Section X, Chemotherapy of Neoplastic Diseases, pp. 1225-1229, 1996.

Hamada et al., "Efficient Total Synthesis of Didemnins A and B", J. Am. Chem. Soc., vol. 111, pp. 669-673 (Jan. 18, 1989).

Jacob L. "General Pharmacologic Principles", Pharmacology (Fourth Edition). Williams and Wilkins Company, 1996. pp. 1-13.

Jiang et al. "Antitumor Activity of Didemnin B in the Human Tumor Stem Cell Assay". Cancer Chemotherapy and Pharmacology, 1983. 11:1-4.

Jou, Gemma et al., "Total Synthesis of Dehydrodidemnin B. Use of Uronium and Phosphonium Salt Coupling Reagents in Peptide Synthesis in Solution," Journal of Organic Chemistry vol. 62, No. 2, pp. 354-366, 1997.

Jouin et al. "Antineoplastic Activity of Didemnin Congeners: Nordidemnin and Modified Chain Analogues". Journal of Medicinal Chemistry. 1991, 34:486-491.

Lobo, C. et al., "Effect of Dehydrodidemnin B on Human Colon Carcinoma Cell Lines," Anticancer Research vol. 17. No. 1A, pp. 333-336, 1997.

Mastbergen et al., "Cytotoxicity and Neurocytotoxicity of Aplidine, a New Marine Anticancer Agent Evaluated Using In vitro Assays," Annals of Oncology, vol. 9, suppl. 2, #131, 1998.

Montgomery et al., Fed. Prac., vol. 44, p. 634 (1987).

Montgomery, D. W., Zukoski, C. F., Transplantation, vol. 40, pp. 49-56 (1985).

Nujien B. et al., Pharmaceutical development of Anticancer Agents derived from Marine Sources, Anti-Cancer Drugs, vol. 11, pp. 793-811, 2000.

Osol A. [Editor] "Chapter 27: Structure-Activity Relationship and Drug Design". Remington's Pharmaceutical Sciences (Sixteenth Edition), 1980. pp. 420-435.

Raymond, Eric et al., "Preliminary Results of a Phase I and Pharmacokinetic Study of Aplidine Given as a 24-hour Infusion Every Weeks in Patients with Solid Tumors and Non Hodgkin's Lymphomas," Proceedings of the American Association for Cancer Research, vol. 41, #3886, 2000.

Rinehart, Kenneth L. et al., "Didemnins and Tunichlorin: Novel Natural Products from the Marine Tunicate Trididemnum Solidum," Journal of Natural Products. vol. 51, No. 1, pp. 1-21, 1988.

Rinehart, Kenneth L., Jr. et al., "Didemnins: Antiviral and Antitumor Depsipeptides from a Caribbean Tunicate," Science, vol. 212, No. 4497, pp. 933-935, 1981.

Rinehart, Kenneth L., Jr. et al., "Antiviral and antitumor compounds from tunicates," Federation Proceedings;vol. 42, No. 1, pp. 87-90 1983.

Rinehart, Jr. et al., Pure and Appl. Chem., vol. 54, pp. 2409-2424 (1982).

Rinehart, "Didemnin and its Biological Properties", Escom, pp. 626-631, (1987).

Rinehart, Jr., J. Am. Chem. Soc. vol. 103, pp. 1857-1859 (1981).

Rinehart et al., "Total Synthesis of Didemnins, A, B, and C", J. Am. Chem. Soc., vol. 109, pp. 6846-6848 (Oct. 28, 1987).

Sakai et a;., "Structure-Activity Relationships of the Didemnins," Journal of Medicinal Chemistry, vol. 39, No. 14, pp. 2819-2834, 1996.

Schmidt et al., "Total Synthesis of the Didemnins-2. Synthesis of Didemnin A, B, C, and Prolyldidemnin A", Tetrahedron Letters, vol. 29, pp. 4407-4408 (1988).

Seebach et al., "Alkylation of Amino Acids Without Loss of the Optical Activity: Preparation of α-Substituted Proline Derivatives. A Case of Self-Reproduction of Chiralty," Journal of the American Chemical Society, vol. 105, No. 16, pp. 5390-5398, 1983.

The Merck Index, Eleventh Ed., p. 489 (1989).

Urdlales et al., "Antiproliferative Effect of Dehydrodidemnin B (DDB), a Depsipeptide Isolated from Mediterranean Tunicates," Cancer Letters, vol. 102, Nos. 1, 2, pp. 31-37, 1996.

Vervoort et al., "Tamandarins A and B: New Cytotoxic Depsipeptides from a Brazilian Ascidian of the Family Didemnidae," The Journal of Organic Chemistry, vol. 65, No. 3, pp. 782-792, 2000.

U.S. Appl. No. 09/622,433.

U.S. Appl. No. 10/130,097.

Broggini et al., "Aplidine blocks VEGF secretion and VEG/VEGF-RI autocrine loop in a human leukemic cell line," Clinical Cancer Research, vol. 6, Supplement, Abstract 214, p. 4509s, NCI-EORTC-AACR Symposium On New Drugs In Cancer Therapy, Nov. 7-10, 2000.

Harris et al., "The World Health Organization Classification of Hematological Malignancies Report of the Clinical Advisory Committee Meeting, Airlie House, Virginia, Nov. 1997," Modern Pathology, vol. 13, No. 2, pp. 193-207, 2000.

Izbicka et al., "Evaluation of molecular targets for aplidine, a novel anticancer agent," Clinical Cancer Research, vol. 6, Supplement, Abstract 213, pp. 4509s, NCI-EORTC-AACR Symposium On New Drigs In Canaer Therapy, Nov. 7-10, 2000.

Izquierdo et al., "Phase I trial of Aplidine (APL) given as a 1 hour (h) intravenous (iv) weekly (wk) infusion in patients (pts) with advanced solid tumors (ST) and lymphoma (NHL)," Clinical Cancer Research, vol. 6, Supplement, Abstract 215, p. 4509s, NCI-EORTC-AACR Symposium On New Drugs In Cancer Therapy, Nov. 7-10, 2000.

Jimeno et al., "A correlation of selective antitumor activities of the marine-derived compound Aplidine using different model systems," Proceedings of the 1999 AACR-NCI-EORTC International Conference, Clinical Cancer Research, vol. 5, Supplement, p. 3791s, Abstract 311, Nov. 16-19, 1999.

Maroun et al., "Phase I study of aplidine in a 5 day bolus q 3 weeks in patients with solid tumors and lymphomas," Clinical Cancer Research, vol. 6, Supplement, Abstract 216, p. 4509s, NCI-EORTC-AACR Symposium On New Drugs In Cancer Therapy, Nov. 7-10, 2000.

Paz-Ares et al., "Phase I clinical and pharmacokinetic study of aplidine, a new marine didemnin, administered as a 24-hour infusion weekly," Clinical Cancer Research, vol. 6, Supplement, Abstract 217, p. 4509s, NCI-EORTC-AACR Symposium On New Drugs In Cancer Therapy, Nov. 7-10, 2000.

Weiss et al., "A Phase II Trial of Didemnin B in Myeloma," Investigational New Drugs, vol. 12, No. 1, pp. 41-43, 1994.

U.S. Appl. No. 09/182,688.

U.S. Appl. No. 10/357,759.

U.S. Appl. No. 10/398,835.

U.S. Appl. No. 10/492,659.

U.S. Appl. No. 10/548,710.

U.S. Appl. No. 11/136,622.

* cited by examiner

Figure 3A (CCRF-CEM)

Figure 3B (SKI-DLCL)

Figure 3C (K562)

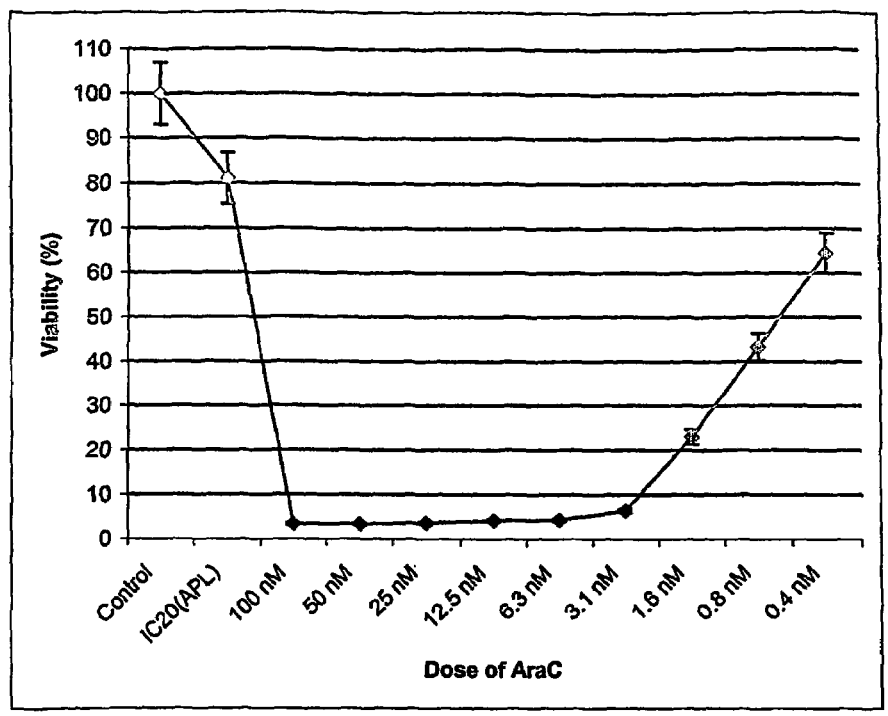
Figure 14A
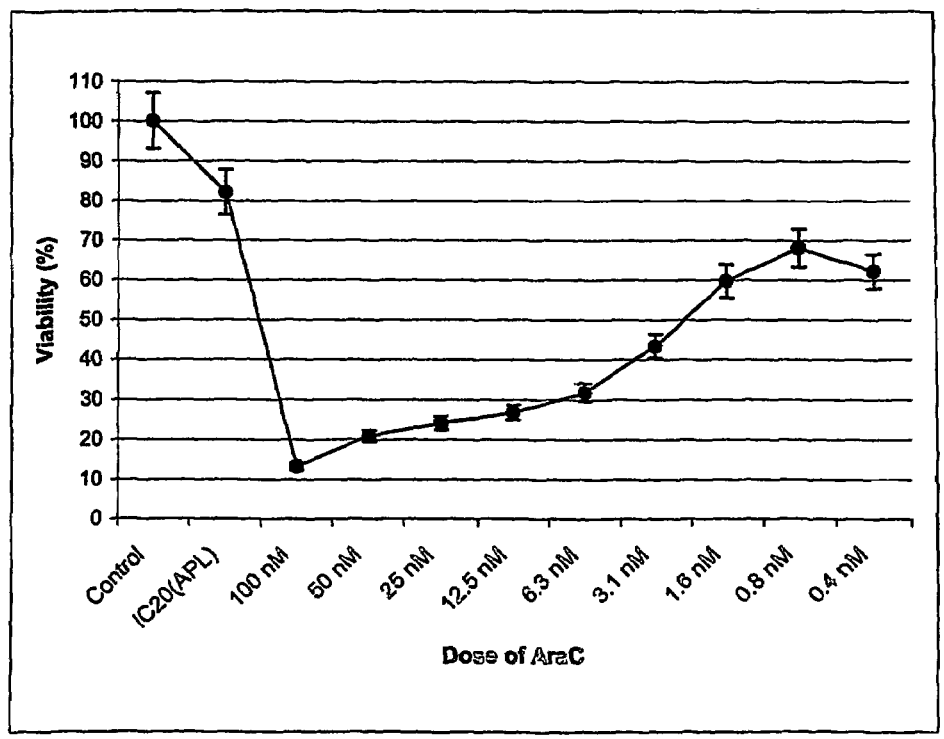
Figure 14B
Figure 14

ANTITUMORAL TREATMENTS

FIELD OF THE INVENTION

The present invention relates to combinations of aplidine or aplidine analogues with other antitumoral agents, and the use of these combinations in the treatment of cancer, in particular in the treatment of leukemias and lymphomas.

BACKGROUND OF THE INVENTION

Aplidine (Dehydrodidemnin B) is a cyclic depsipeptide that was isolated from a Mediterranean marine tunicate, *Aplidium albicans,* and it is the subject of WO 9109485. It is related to compounds known as didemnins, and has the following structure:

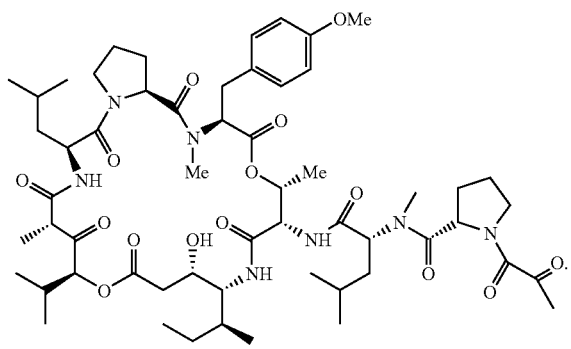

More information on aplidine, aplidine analogues, their uses, formulations and synthesis can be found in patent applications WO 98 1352, WO 99 42125, WO 01 76616, WO 01 35974, WO 02 30441 and WO 02 02596. We incorporate by specific reference the content of each of these PCT texts.

In both animal and human preclinical studies and in clinical Phase I studies this agent has been shown to have cytotoxic potential against a broad spectrum of tumor types including leukemia and lymphoma. See for example:

Faircloth, G. et al.: "Dehydrodidemnin B (DDB) a new marine derived anticancer agent with activity against experimental tumour models", 9th NCI-EORTC Symp New Drugs Cancer Ther (March 12-15, Amsterdam) 1996, Abst 111;

Faircloth, G. et al.: "Preclinical characterization of aplidine, a new marine anticancer depsipeptide", *Proc Amer Assoc Cancer Res* 1997, 38: Abst 692;

Depenbrock H, Peter R, Faircloth G T, Manzanares I, Jimeno J, Hanauske A R.: "In vitro activity of Aplidine, a new marine-derived anti-cancer compound, on freshly explanted clonogenic human tumour cells and haematopoietic precursor cells" *Br. J. Cancer,* 1998; 78: 739-744;

Faircloth G, Grant W, Nam S, Jimeno J, Manzanares I, Rinehart K.: "Schedule-dependency of Aplidine, a marine depsipeptide with antitumor activity'", *Proc. Am. Assoc. Cancer Res.* 1999; 40: 394;

Broggini M, Marchini S, D'Incalci M, Taraboletti G, Giavazzi R, Faircloth G, Jimeno J.: "Aplidine blocks VEGF secretion and VEGF/VEGF-R1 autocrine loop in a human leukemic cell line", *Clin Cancer Res* 2000; 6 (suppl): 4509;

Erba E, Bassano L, Di Liberti G, Muradore I, Chiorino G, Ubezio P, Vignati S, Codegoni A, Desiderio M A, Faircloth G, Jimeno J and D'Incalci M.: "Cell cycle phase perturbations and apoptosis in tumour cells induced by aplidine", *Br J Cancer* 2002; 86: 1510-1517;

Paz-Ares L, Anthony A, Pronk L, Twelves C, Alonso S, Cortes-Funes H, Celli N, Gomez C, Lopez-Lazaro L, Guzman C, Jimeno J, Kaye S.: "Phase I clinical and pharmacokinetic study of aplidine, a new marine didemnin, administered as 24-hour infusion weekly" *Clin. Cancer Res.* 2000; 6 (suppl): 4509;

Raymond E, Ady-Vago N, Baudin E, Ribrag V, Faivre S, Lecot F, Wright T, Lopez Lazaro L, Guzman C, Jimeno J, Ducreux M, Le Chevalier T, Armand J P.: "A phase I and pharmacokinetic study of aplidine given as a 24-hour continuous infusion every other week in patients with solid tumor and lymphoma", *Clin. Cancer Res.* 2000; 6 (suppl): 4510;

Maroun J, Belanger K, Seymour L, Soulieres D, Charpentier D, Goel R, Stewart D, Tomiak E, Jimeno J, Matthews S.:"Phase I study of aplidine in a 5 day bolus q 3 weeks in patients with solid tumors and lymphomas", *Clin. Cancer Res.* 2000; 6 (suppl): 4509;

Izquierdo M A, Bowman A, Martinez M, Cicchella B, Jimeno J, Guzman C, Germa J, Smyth J.: "Phase I trial of Aplidine given as a 1 hour intravenous weekly infusion in patients with advanced solid tumors and lymphoma", *Clin. Cancer Res.* 2000; 6 (suppl): 4509.

Mechanistic studies indicate that aplidine can block VEGF secretion in ALL-MOLT4 cells and in vitro cytotoxic activity at low concentrations (5nM) has been observed in AML and ALL samples from pediatric patients with de novo or relapsed ALL and AML. Aplidine appears to induce both a G1, and a G2 arrest in drug treated leukemia cells in vitro. Apart from down regulation of the VEGF receptor, little else is known about the mode(s) of action of aplidine.

In phase I clinical studies with aplidine, L-carnitine was given as a 24 hour pretreatment or co-administered to prevent myelotoxicity, see for example WO 02 30441. Co-administration of L-carnitine was proven to be able to improve the recovery of the drug induced muscular toxicity and has allowed for dose escalation of aplidine.

Thus in clinical Phase I studies aplidine was not myelotoxic at maximum tolerated doses, except for mild lymphopenia. These characteristics make aplidine a potentially useful agent for the treatment of leukemia. Adding aplidine to the current chemotherapy for leukemia could improve efficacy without the necessity of dose reductions of drugs with proven antileukemic activity, because of increased myelotoxicity. This seems especially relevant for the treatment of relapsed ALL and newly diagnosed and relapsed AML, since these are diseases with a relatively poor prognosis, which are currently being treated with myelotoxic drug combinations.

SUMMARY OF THE INVENTION

We have for the first time established that aplidine and aplidine analogues potentiate other anticancer agents and therefore can be successfully used in combination therapy for the treatment of cancer. This invention is directed to pharmaceutical compositions, pharmaceutical dosage forms, kits and methods for the treatment of cancer using these combination therapies.

In accordance with one aspect of this invention, we provide effective combination therapies based on aplidine and aplidine analogues, using other drugs which are effective in the treatment of cancer. Preferably the other drug is effective in the treatment of leukemia and/or lymphoma. Most preferably the other drug is selected from the group consisting of methotrexate, cytosine arabinoside, mitoxantrone, vinblastine, methylprednisolone and doxorubicin.

In another embodiment the invention encompasses a method of treating primary and/or metastatic cancer comprising administering to a patient in need of such treatment a therapeutically effective amount of aplidine or an aplidine analogue, or a pharmaceutically acceptable prodrug, salt, solvate or hydrate thereof, and a therapeutically effective amount of another drug which is effective in the treatment of cancer or a pharmaceutically acceptable prodrug, salt, solvate or hydrate thereof, administered prior, during, or after administering aplidine or aplidine analogue.

Preferably the other drug is effective in the treatment of leukemia and/or lymphoma. Most preferably the other drug is selected from the group consisting of methotrexate, cytosine arabinoside, mitoxantrone, vinblastine, methylprednisolone and doxorubicin. The other drugs may form part of the same composition, or be provided as a separate composition for administration at the same time or at a different time.

The cancer to be treated is preferably a leukemia or a lymphoma, most preferably ALL, AML, CML, MML or CLL.

In another aspect the invention encompasses a method of increasing the therapeutic efficacy of a drug effective in the treatment of cancer, preferably a drug effective in the treatment of leukemia and/or lymphoma, most preferably a drug selected from the group consisting of methotrexate, cytosine arabinoside, mitoxantrone, vinblastine, methylprednisolone and doxorubicin, or a pharmaceutically acceptable prodrug, salt, solvate or hydrate thereof, which comprises administering to a patient in need thereof an amount of aplidine or an aplidine analogue, or a pharmaceutically acceptable prodrug, salt, solvate or hydrate thereof. Aplidine or the aplidine analogue is administered prior, during, or after administering the other drug.

Aplidine or an aplidine analogue is able to increase the therapeutic efficacy of some cancer drugs. In one aspect, the result is synergism, rather than additive. Such synergistic combinations represent a preferred aspect of the present invention. Synergism may be indicated by use of the Chou-Talalay method, or other methods. In other instances, antagonism may be found.

In a further aspect the invention encompasses a pharmaceutical composition comprising aplidine or an aplidine analogue, or a pharmaceutically acceptable prodrug, salt, solvate or hydrate thereof, and another drug effective in the treatment of cancer. Preferably the other drug is effective in the treatment of leukemia and/or lymphoma. Most preferably the other drug is selected from the group consisting of methotrexate, cytosine arabinoside, mitoxantrone, vinblastine, methylprednisolone and doxorubicin.

The invention also encompasses a kit for use in the treatment or prevention of cancer which comprises a dosage form of aplidine or an aplidine analogue, or a pharmaceutically acceptable prodrug, salt, solvate or hydrate thereof, a dosage form of another drug effective in the treatment of cancer, or a pharmaceutically acceptable prodrug, salt, solvate or hydrate thereof, and instructions for the use of each actor in combination for the treatment or prevention of cancer. Preferably the other drug is effective in the treatment of leukemia and/or lymphoma. Most preferably the other drug is selected from the group consisting of methotrexate, cytosine arabinoside, mitoxantrone, vinblastine, methylprednisolone and doxorubicin.

In a further aspect, the invention is directed to the use of aplidine for the treatment of chronic lymphocytic leukemia.

DETAILED DESCRIPTION OF THE INVENTION

Figure 1:
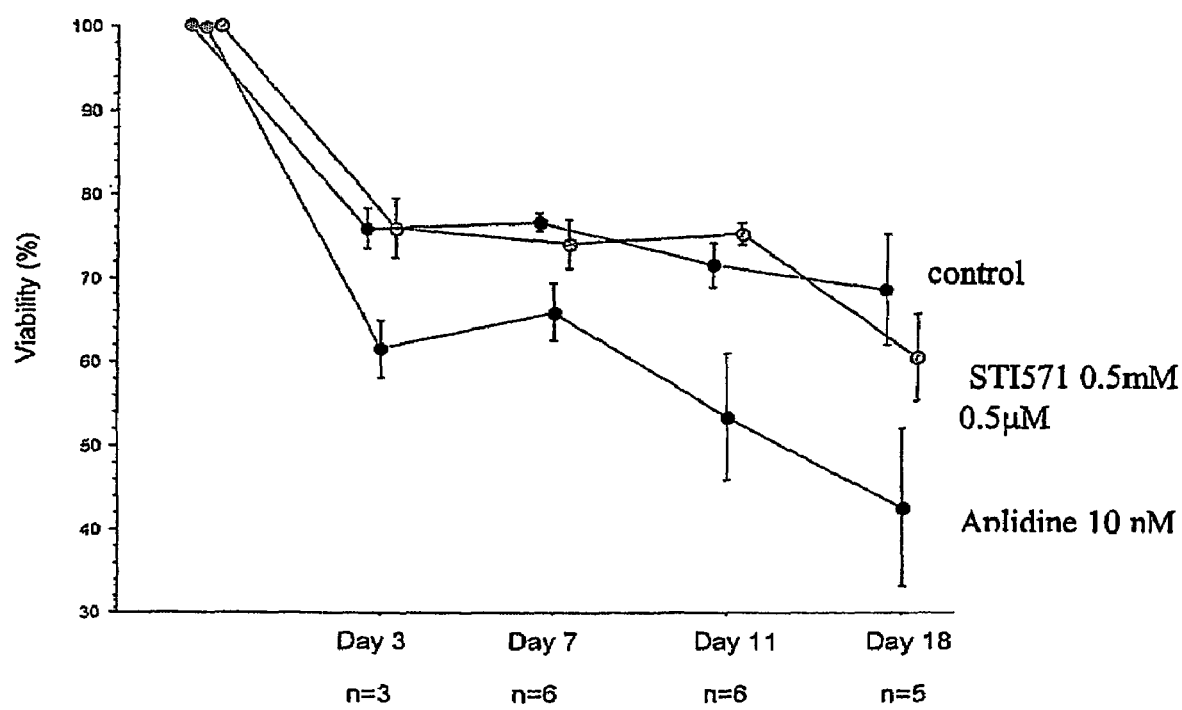
FIG. 1. Aplidine inhibits growth of CLL cells in culture

By cancer it is meant to include tumors, neoplasias, and any other malignant tissue or cells. The present invention is directed to the use of aplidine or an aplidine analogue in combination for the treatments of cancer in general, but more preferably for the treatment of different leukemias and lymphomas.

In order to study the possible potentiation of other anticancer agents with aplidine we have initiated a systematic study of drug combinations for possible use in leukemias and lymphomas. Aplidine was found to be an effective in vitro cytotoxic agent against primary cells from a patient with preB-ALL (DM4) as well as against fresh cells obtained from six chronic lymphocytic leukemia (CLL) patients. The $IC_{50}$ value was 10 nM for 3 day exposure with the DM4 line and after a 11 day exposure with the primary CLL samples.

Drug combination studies were carried out on established cell lines rather than primary cells. We studied three cell lines viz. K562, CCRF-CEM and SKI-DLCL representing acute myeloid leukemia, lymphoblastic lymphoma and diffuse B cell large cell lymphoma respectively. The data in the examples show that Aplidine potentiates the effect of methotrexate, cytosine arabino side, mitoxantrone, vinblastine, methylprednisolone as well as doxorubicin in K562, CCRF-CEM and SKI-DLCL cells by lowering the $IC_{50}$s for the drugs.

Thus we have found that aplidine is a potent cytotoxic agent against cells of several hematologic mailgnancies. Significantly, we have established for the first time that aplidine inhibits growth of CLL cells in culture. We also found that aplidine enhances the cytotoxicity of agents used in the treatment of leukemias, such as methotrexate (MTX), cytosine arabonoside (AraC), mitoxantrone (Mitox), vinblastine (Vinb), methylprednisolone (Metpred) and doxorubicin (DOX).

Leukemia is classified by how quickly it progresses. Acute leukemia is fast-growing and can overrun the body within a few weeks or months. By contrast, chronic leukemia is slow-growing and progressively worsens over years.

The blood-forming (hematopoietic) cells of acute leukemia remain in an immature state, so they reproduce and accumulate very rapidly. Therefore, acute leukemia needs to be treated immediately, otherwise the disease may be fatal within a few months. Fortunately, some subtypes of acute leukemia respond to available therapies and they are curable. Children often develop acute forms of leukemia, which are managed differently from leukemia in adults.

In chronic leukemia, the blood-forming cells eventually mature, or differentiate, but they are not "normal". They remain in the bloodstream much longer than normal white blood cells, and they are unable to combat infection well.

Leukemia also is classified according to the type of white blood cell that is multiplying—that is, lymphocytes (immune system cells), granulocytes (bacteria-destroying cells), or monocytes (macrophage-forming cells). If the abnormal white blood cells are primarily granulocytes or monocytes, the leukemia is categorized as myelogenous, or myeloid, leukemia. On the other hand, if the abnormal blood cells arise from bone marrow lymphocytes, the cancer is called lymphocytic leukemia.

Other cancers, known as lymphomas, develop from lymphocytes within the lymph nodes, spleen, and other organs. Such cancers do not originate in the bone marrow and have a biological behavior that is different from lymphocytic leukemia.

There are over a dozen different types of leukemia, but four types occur most frequently. These classifications are based upon whether the leukemia is acute versus chronic and myelogenous versus lymphocytic, that is:

Acute myelogenous leukemia (AML): also known as acute nonlymphocytic leukemia (ANLL)—is the most common form of adult leukemia. Most patients are of retirement age (average age at diagnosis=65 years), and more men are affected than women. Fortunately, because of recent advances in treatment, AML can be kept in remission (lessening of the disease) in approximately 60% to 70% of adults who undergo appropriate therapy. Initial response rates are approximately 65-75% but the overall cure rates are more on the order of 40-50%.

Chronic myelogenous leukemia (CML) is known as a myeloproliferative disorder—that is, it is a disease in which bone marrow cells proliferate (multiply) outside of the bone marrow tissue. CML is easy to diagnose, since it has a genetic peculiarity, or marker, that is readily identifiable under a microscope. About 95% of CML patients have a genetic translocation between chromosomes 9 and 22 in their leukemic cells. The Philadelphia chromosome causes uncontrolled reproduction and proliferation of all types of white blood cells and platelets (blood clotting factors). CML is not yet curable by standard methods of chemotherapy or immunotherapy.

Acute lymphocytic leukemia (ALL)—also known as acute lymphoblastic leukemia—is a malignant disease caused by the abnormal growth and development of early nongranular white blood cells, or lymphocytes. The leukemia originates in the blast cells of the bone marrow (B-cells), thymus (T-cells), and lymph nodes. ALL occurs predominantly in children, peaking at 4 years of age.

Chronic lymphocytic leukemia (CLL) is the most common leukemia in North America and in Europe. It is a disease of older adults and is very rare among people who are younger than 50 years of age. Men with CLL outnumber women by a 2-to-1 average. CLL is thought to result from the gradual accumulation of mature, long-lived lymphocytes. Therefore, this cancer is caused not so much by overgrowth as it is by the extreme longevity and build-up of malignant cells. Although the rate of accumulation varies among individuals, the extensive tumor burden eventually causes complications in all CLL patients.

The compositions of the present invention may comprise both components (drugs) in a single pharmaceutically acceptable formulation. Alternatively, the components may be formulated separately and administered in combination with one another. Various pharmaceutically acceptable formulations well known to those of skill in the art can be used in the present invention. Selection of an appropriate formulation for use in the present invention can be performed routinely by those skilled in the art based upon the mode of administration and the solubility characteristics of the components of the composition.

Examples of pharmaceutical compositions containing Aplidine or an aplidine analogue include liquid (solutions, suspensions or emulsions) with suitable composition for intravenous administration, and they may contain the pure compound or in combination with any carrier or other pharmacologically active compounds. Solubilised aplidine shows substantial degradation under heat and light stress testing conditions, and a lyophilised dosage form was developed, see WO99/42125 incorporated herein by reference.

Administration of aplidine or compositions of the present invention is based on a Dosing Protocol preferably by intravenous infusion. We prefer that infusion times of up to 72 hours are used, more preferably 1 to 24 hours, with about 1, about 3 or about 24 hours most preferred. Short infusion times which allow treatment to be carried out without an overnight stay in hospital are especially desirable. However, infusion may be around 24 hours or even longer if required. Infusion may be carried out at suitable intervals with varying patterns, illustratively once a week, twice a week, or more frequently per week, repeated each week optionally with gaps of typically one week.

The correct dosage of the compounds of the combination will vary according to the particular formulation, the mode of application and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose. Further guidance for the administration of aplidine is given in WO 0135974 which is incorporated herein by reference in its entirety.

For the present invention, analogues of aplidine can be used in place of APL, aplidine itself. Typically such compounds are as defined in WO 0202596. Examples of compounds for the present invention include the preferred compounds given in WO 0202596, and in particular we import into this patent specification the discussion of preferred compounds and related aspects given in WO 0202596. More preferably, the analogues are structurally close to aplidine, and usually differ from aplidine in respect of one amino acid or the terminal sidechain. The different amino acid can be in the cyclic part of the molecule or in the sidechain. Many examples of such compounds are given in WO 0202596, and they are candidates for use in the present invention.

EXAMPLE

Example 1

Aplidine was tested against various primary cells from patients with hematologic malignancies. The cells used were:
fresh cells obtained from six chronic lymphocytic leukemia patients
primary cell from a patient with preB-ALL (DM4)

Patient samples were obtained with prior consent and CLL cells were isolated by density gradient centrifugation over histopaque. The media used was RPMI supplemented with 10% autologous serum and L-glutamine. The cultures were incubated with 10 nM aplidine and cell viability was measured days 3, 7,11 and 18 and compared with viability of untreated cells and STI 571 (0.5 mM).

Figure 2:
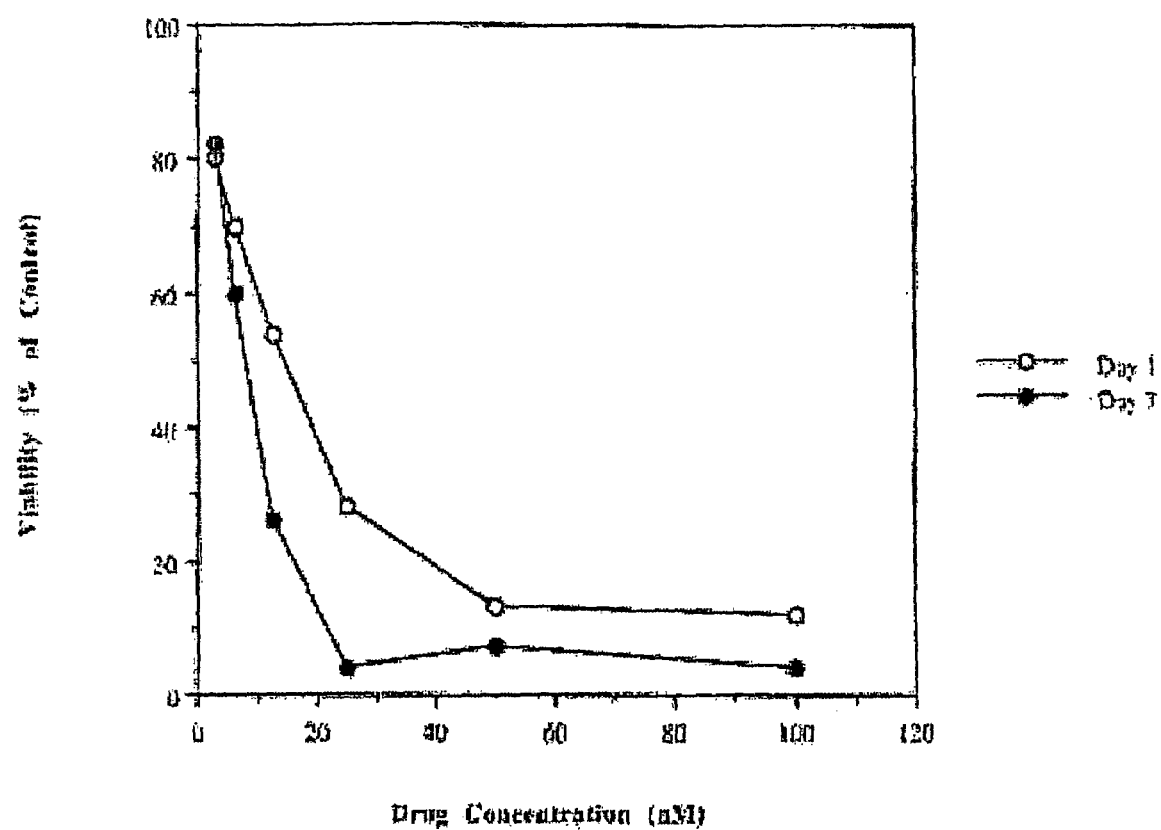
FIG. 2. Aplidine is a potent inhibitor of preB-ALL cells in culture

The results of these studies are shown in FIGS. 1-2.

Example 2

In order to study the possible potentiation of other anticancer agents we undertook a study of drug combinations for possible use in leukemias and lymphomas.

Drug combination studies were carried out on established cell lines rather than primary cells. We studied three cell lines, viz. K562 as a model for acute myeloid leukemia, CEM representing acute lymphocytic leukemia and SKI-DLCL representing diffuse large cell lymphoma. Combination studies with IC20 and IC 50 dose of aplidine with a dose range of methotrexate, cytosine arabinoside and doxorubicin were tested to determine if aplidine could potentiate the effect of these drugs.

The results are shown in table 1:

|  | Additional Drug | | |
| --- | --- | --- | --- |
|  | IC50 Dox | IC50 MTX | IC50 Ara-C |
| No Aplidine | 18 nM | 5 nM | 30 nM |
| IC$_{20}$ Aplidine (0.5 nM) | 1 nM | 500 pM | 6 nM |

$p < 0.01, p < 0.05, p < 0.05$

Clearly, these data show that aplidine potentiates the effect of doxorubicin, methotrexate and cytosine arabinoside by lowering very significantly the IC$_{50}$s for the drugs.

Example 3

Figure 3:
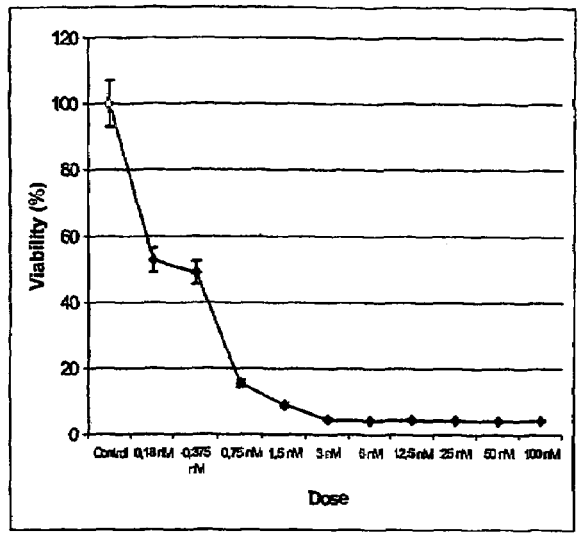
FIG. 3. The cytotoxic dose-response curve of CCRF-CEM (FIG. 3A), SKI-DLCL (FIG. 3B) and K562 (3C) cells following aplidine treatment for 96 hours FIG. 4. Chou-Talalay analysis of combination of aplidine and AraC in CCRF-CEM cells FIG. 5. Chou-Talalay analysis of combination of aplidine and AraC in SKI-DLCL cells FIG. 6. Chou-Talalay analysis of combination of aplidine and mitoxantrone in CCRF-CEM cells FIG. 7. Chou-Talalay analysis of combination of aplidine and mitoxantrone in SKI-DLCL cells FIG. 8. Chou-Talalay analysis of combination of aplidine and methotrexate in CCRF-CEM cells FIG. 9. Chou-Talalay analysis of combination of aplidine and doxorubicin in CCRF-CEM cells FIG. 10. Chou-Talalay analysis of combination of aplidine and vinblastine in CCRF-CEM cells FIG. 11. Chou-Talalay analysis of combination of aplidine and doxorubicin in SKI-DLCL cells FIG. 12. Chou-Talalay analysis of combination of aplidine and vinblastine in SKI-DLCL cells FIG. 13. Chou-Talalay analysis of combination of aplidine and methylprednisolone in SKI-DLCL cells FIG. 14. Combination of $IC_{20}$ of aplidine lowered the $IC_{50}$ of AraC in CCRF-CEM (FIG. 12A) and SKI-DLCL (FIG. 12B) cells after incubation for 96 hours FIG. 15. The effect of aplidine on in vivo tumor size as a single agent and in combination with AraC
Figure 3:
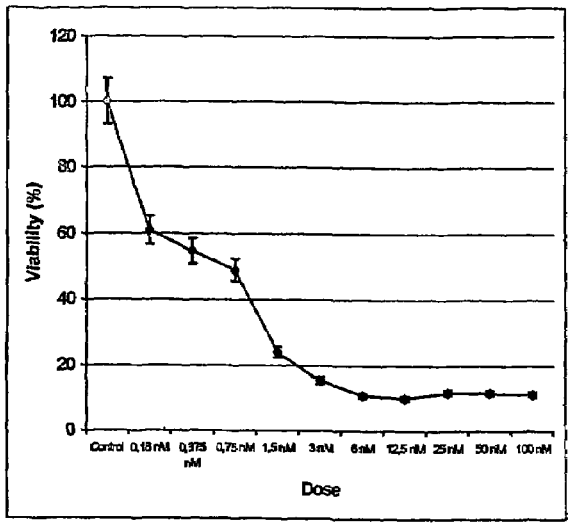
Figure 3:
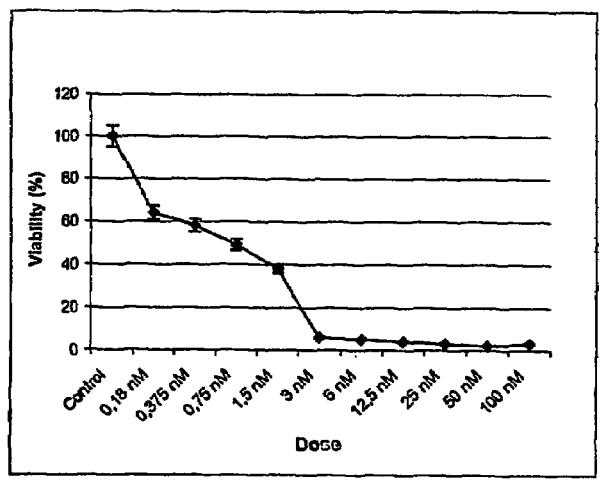

In vitro Studies to Determine the Effect of Aplidine as a Single Agent on CCRF-CEM, SKI-DLCL and K562 Cell Lines CCRF-CEMS, SKI-DLCL and K562 cells are maintained in RPMI 1640 supplemented with 10% FCS. To determine the cytotoxic effect of aplidine on all cell lines and to obtain the IC$_{50}$ of aplidine in these cell lines, cells were plated into 96 well plates and incubated for 96 hours in humidified and 5% CO2 containing incubator. Cell viability is measured by XTT assay in an automated plate reader. We found aplidine to be cytotoxic to all cell lines with an IC$_{50}$ dose of 0.5-1.0 nM (FIG. 3).

Example 4

Studies on in vitro Effect of Aplidine+Drug Combination with Fixed Doses of IC$_{50}$:IC$_{50}$ on All Cell Lines Methotrexate, cytosine arabinoside C (ara-C), mitoxantrone, methylprednisolone, vinblastine and doxorubicin were tested in combination with aplidine.

Chou-Talalay analysis was used to analyze the drug combinations. When Combination Index (CI) obtained by this analysis is less than 1, the drugs are synergistic; when CI is 1, the drugs are additive; and, if CI is greater than 1, the drugs are antagonistic.

All the citotoxicity studies were performed by using XTT or MTS. We first determined the IC$_{50}$ dose of these drugs in SKI-DLCL, CCRF-CEM and K562 cell lines. We investigated drug combinations using IC$_{50}$(Aplidine):IC$_{50}$(DrugX) fixed ratio.

In table 2 is shown the combination of aplidine and Ara-C with the dose of (IC$_{50}$:IC$_{50}$) in CCRF-CEM cells.

TABLE 2

| Ratio | Dose of APL | Dose of AraC | Viability (% of control) |
| --- | --- | --- | --- |
| Control | 0 | 0 | 100 |
| IC50(APL) | 0.5 nM | 0 | 52.7 |
| IC50(AraC) | 0 | 10 nM | 56.4 |
| ×16 | 8 nM | 160 nM | 4.7 |
| ×8 | 4 nM | 80 nM | 7.9 |
| ×4 | 2 nM | 40 nM | 7.6 |
| ×2 | 1 nM | 20 nM | 7.8 |
| IC50:IC50 | 0.5 nM | 10 nM | 10.6 |
| ×½ | 0.25 nM | 5 nM | 16.2 |
| ×¼ | 1.125 nM | 2.5 nM | 36.7 |
| ×⅛ | 0.0625 nM | 1.25 nM | 70.8 |

Figure 4:
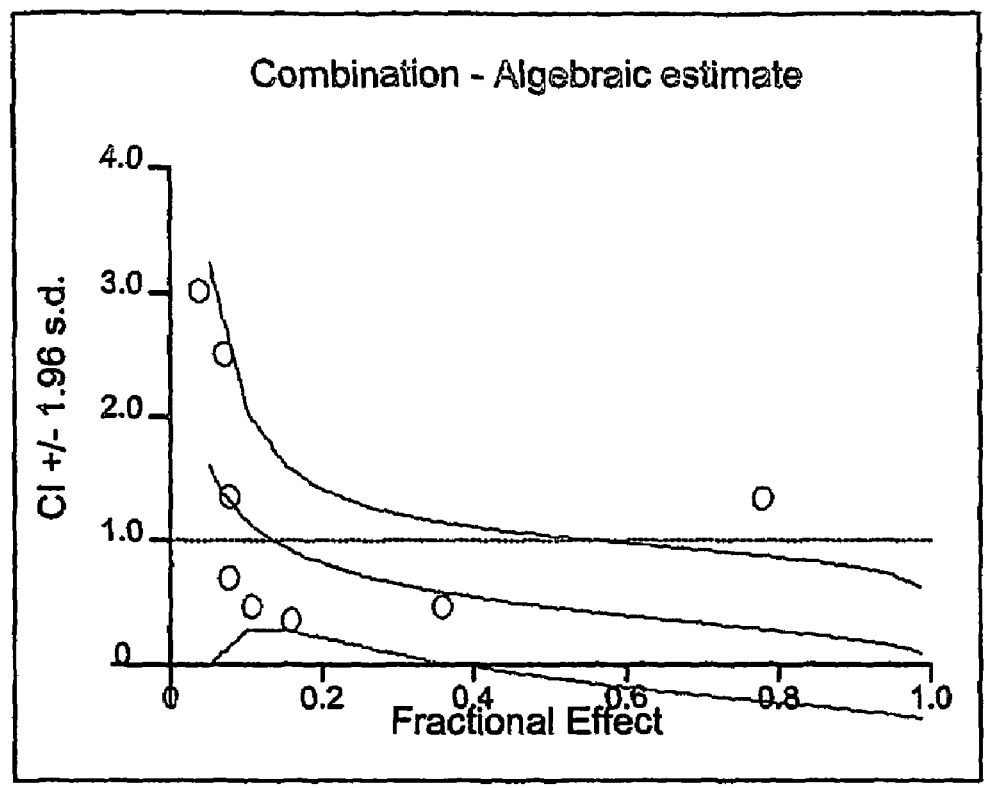
Figure 4:
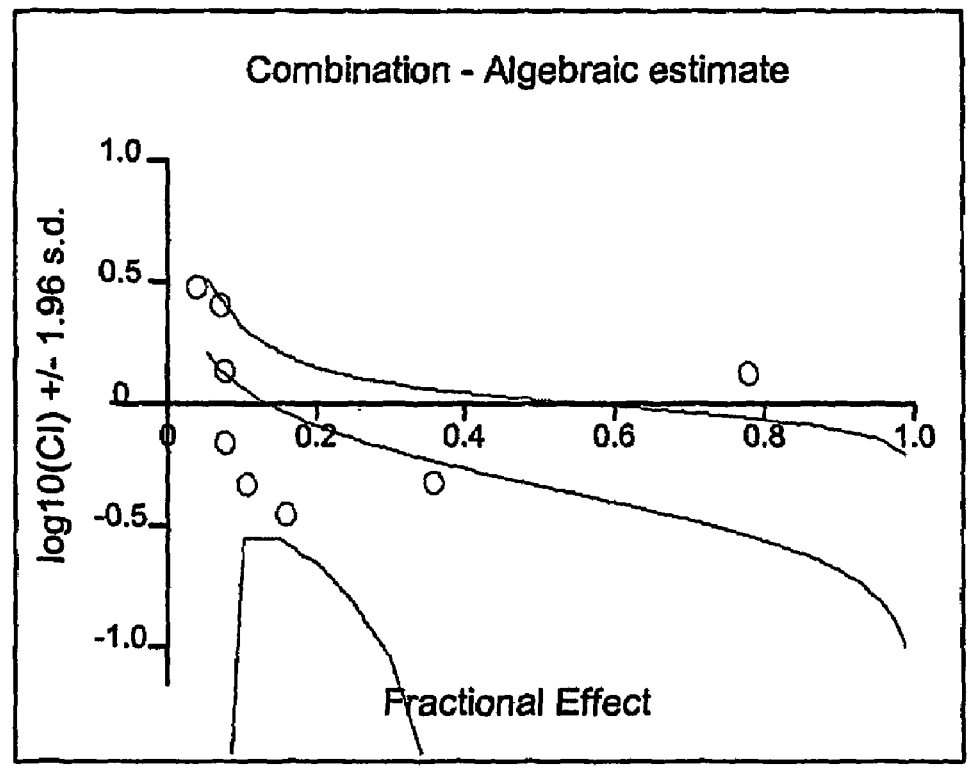

The results of Chou-Talalay analysis of combination of aplidine and Ara-C in CCRF-CEM cells can be seen in FIG. 4. The CI for this combination in CCRF-CEM cells is 0.469.

In table 3 is shown the combination of aplidine and Ara-C with the dose of (IC$_{50}$:IC$_{50}$) in SKI-DLCL cells.

TABLE 3

| Ratio | Dose of APL | Dose of AraC | Viability (% of control) |
| --- | --- | --- | --- |
| Control | 0 | 0 | 100 |
| IC50(APL) | 0.5 nM | 0 | 50 |
| IC50(AraC) | 0 | 30 nM | 50 |
| ×16 | 8 nM | 480 nM | 12 |
| ×8 | 4 nM | 240 nM | 10.7 |
| ×4 | 2 nM | 120 nM | 14.1 |
| ×2 | 1 nM | 60 nM | 17.4 |
| IC50:IC50 | 0.5 nM | 30 nM | 23.1 |
| ×½ | 0.25 nM | 15 nM | 25.4 |
| ×¼ | 1.125 nM | 7.5 nM | 25.5 |
| ×⅛ | 0.0625 nM | 3.75 nM | 50.8 |

Figure 5:
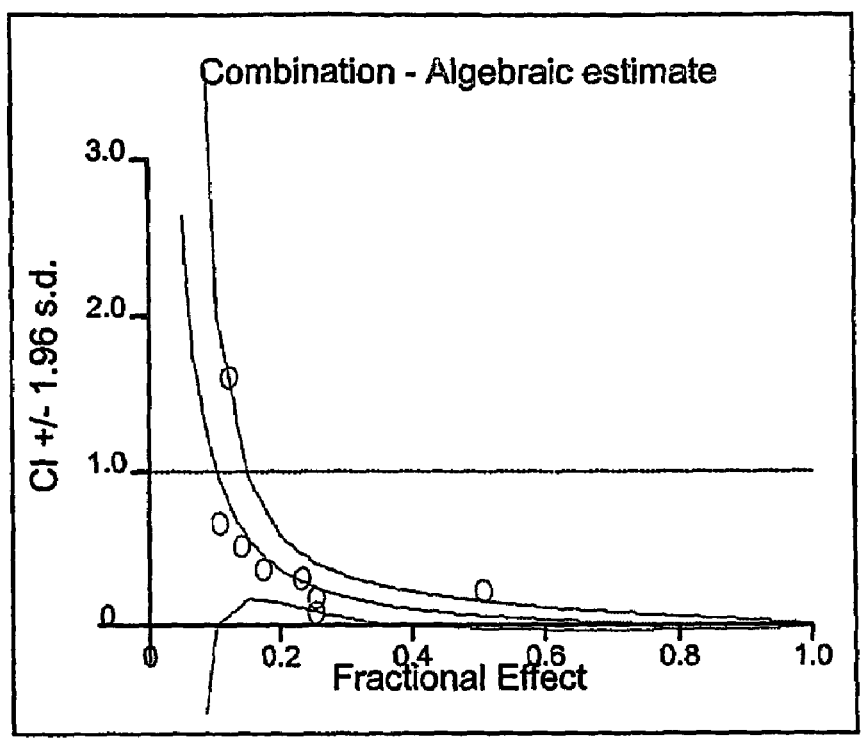
Figure 5:
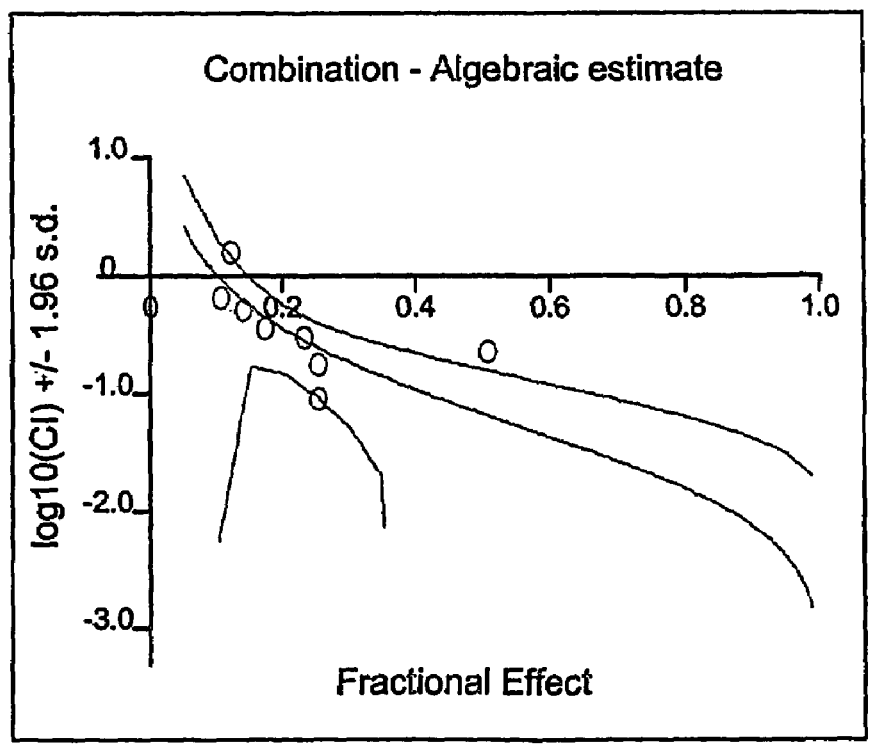

The results of Chou-Talalay analysis of combination of aplidine and Ara-C in SKI-DLCL cells can be seen in FIG. 5. The CI for this combination in SKI-DLCL cells is 0.306.

In table 4 is shown the combination of aplidine and Ara-C with the dose of (IC$_{50}$:IC$_{50}$) in K562 cells.

| Ratio | Dose of APL | Dose of AraC | Viability (% of control) |
|---|---|---|---|
| Control | 0 | 0 | 100 |
| IC50(APL) | 1 nM | 0 | 50 |
| IC50(AraC) | 0 | 30 nM | 50 |
| ×16 | 16 nM | 480 nM | 11.8 |
| ×8 | 8 nM | 240 nM | 15.2 |
| ×4 | 4 nM | 120 nM | 15.5 |
| ×2 | 2 nM | 60 nM | 17 |
| IC50:IC50 | 1 nM | 30 nM | 22.1 |
| ×½ | 0.5 nM | 15 nM | 25.6 |
| ×¼ | 0.25 nM | 7.5 nM | 31.1 |
| ×⅛ | 0.125 nM | 3.75 nM | 44.2 |

The CI for this combination in K562 cells is 0.502.

In table 5 is shown the combination of aplidine and mitoxantrone with the dose of ($IC_{50}$:$IC_{50}$) in CCRF-CEM cells.

| Ratio | Dose of APL | Dose of Mitoxantrone | Viability (% of control) |
|---|---|---|---|
| Control | 0 | 0 | 100 |
| IC50(APL) | 0.5 nM | 0 | 50 |
| IC50(Mitox) | 0 | 30 nM | 56 |
| ×16 | 8 nM | 480 nM | 9.9 |
| ×8 | 4 nM | 240 nM | 11.6 |
| ×4 | 2 nM | 120 nM | 11.9 |
| ×2 | 1 nM | 60 nM | 13.8 |
| IC50:IC50 | 0.5 nM | 30 nM | 20.6 |
| ×½ | 0.25 nM | 15 nM | 39.7 |
| ×¼ | 1.125 nM | 7.5 nM | 60.7 |
| ×⅛ | 0.0625 nM | 3.75 nM | 76.5 |

Figure 6:
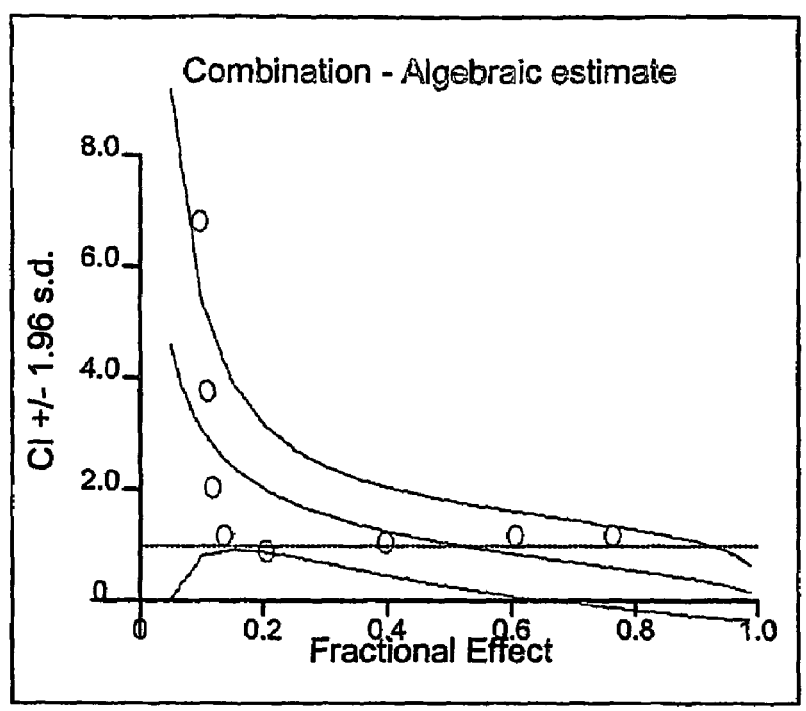
Figure 6:
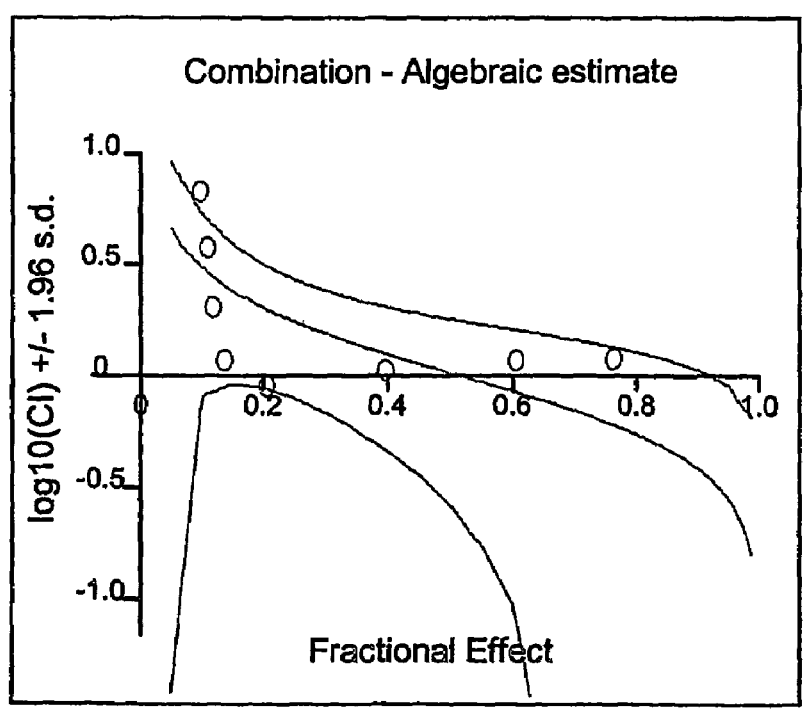

The results of Chou-Talalay analysis of combination of aplidine and mitoxantrone in CCRF-CEM cells can be seen in FIG. 6. The CI for this combination in CCRF-CEM cells is 0.911.

In table 6 is shown the combination of aplidine and mitoxantrone with the dose of ($IC_{50}$:$IC_{50}$) in SKI-DLCL cells.

| Ratio | Dose of APL | Dose of Mitoxantrone | Viability (% of control) |
|---|---|---|---|
| Control | 0 | 0 | 100 |
| IC50(APL) | 0.5 nM | 0 | 50 |
| IC50(Mitox) | 0 | 5 nM | 50 |
| ×16 | 8 nM | 80 nM | 17 |
| ×8 | 4 nM | 40 nM | 29 |
| ×4 | 2 nM | 20 nM | 22.6 |
| ×2 | 1 nM | 10 nM | 19.9 |
| IC50:IC50 | 0.5 nM | 5 nM | 32.2 |
| ×½ | 0.25 nM | 2.5 nM | 53.1 |
| ×¼ | 1.125 nM | 1.25 nM | 58.6 |
| ×⅛ | 0.0625 nM | 0.625 nM | 70.1 |

Figure 7:
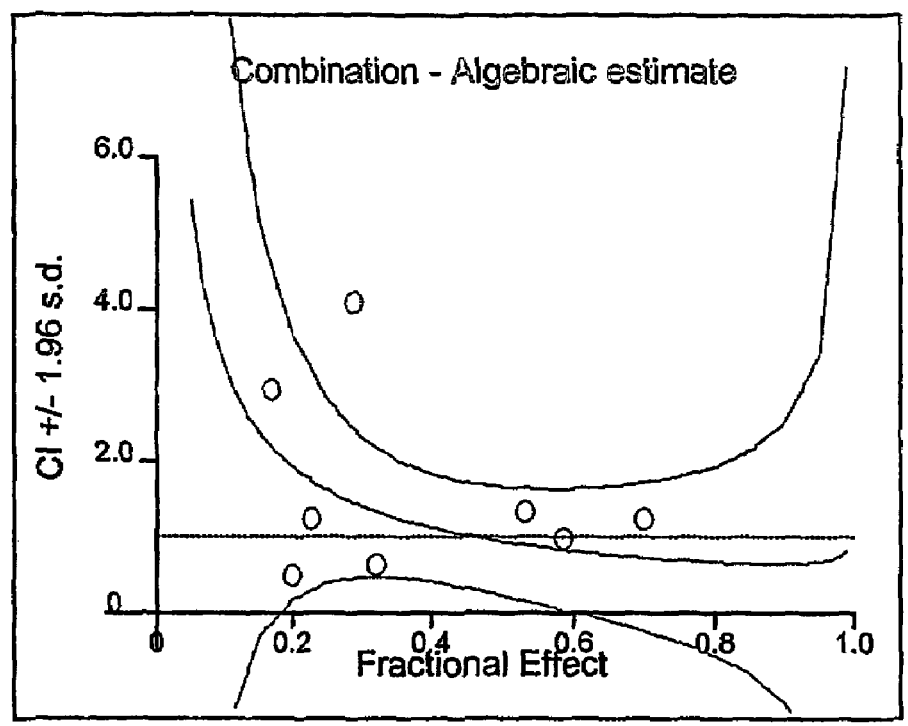
Figure 7:
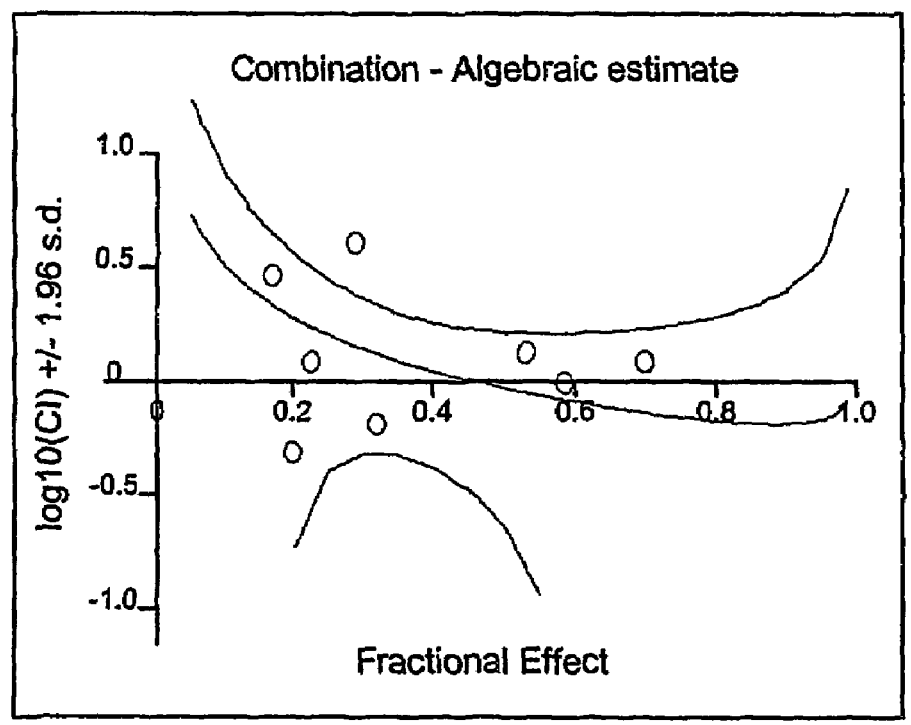

The results of Chou-Talalay analysis of combination of aplidine and mitoxantrone in SKI-DLCL cells can be seen in FIG. 7. The CI for this combination in SKI-DLCL cells is 0.646.

In table 7 is shown the combination of aplidine and mitoxantrone with the dose of ($IC_{50}$:$IC_{50}$) in K562cells.

| Ratio | Dose of APL | Dose of Mitoxantrone | Viability (% of control) |
|---|---|---|---|
| Control | 0 | 0 | 100 |
| IC50(APL) | 1 nM | 0 | 50 |
| IC50(Mitox) | 0 | 7.5 nM | 50.7 |
| ×16 | 16 nM | 120 nM | 9.9 |
| ×8 | 8 nM | 60 nM | 11.6 |
| ×4 | 4 nM | 30 nM | 11.9 |
| ×2 | 2 nM | 15 nM | 13.8 |
| IC50:IC50 | 1 nM | 7.5 nM | 20.6 |
| ×½ | 0.5 nM | 3.75 nM | 39.7 |
| ×¼ | 0.25 nM | 1.8 nM | 60.7 |
| ×⅛ | 0.125 nM | 0.9 nM | 76.5 |

The CI for this combination in K562 cells is 0.487.

In table 8 is shown the combination of alidine and mthotrexate with the dose of ($IC_{50}$:$IC_{50}$) in CCRF-CEM cells.

| Ratio | Dose of APL | Dose of Metotrexate | Viability (% of control) |
|---|---|---|---|
| Control | 0 | 0 | 100 |
| IC50(APL) | 0.5 nM | 0 | 50 |
| IC50(MTX) | 0 | 10 nM | 50 |
| ×16 | 8 nM | 160 nM | 5 |
| ×8 | 4 nM | 80 nM | 13 |
| ×4 | 2 nM | 40 nM | 11 |
| ×2 | 1 nM | 20 nM | 12 |
| IC50:IC50 | 0.5 nM | 10 nM | 20 |
| ×½ | 0.25 nM | 5 nM | 30 |
| ×¼ | 1.125 nM | 2.5 nM | 88 |
| ×⅛ | 0.0625 nM | 1.25 nM | 100 |

Figure 8:
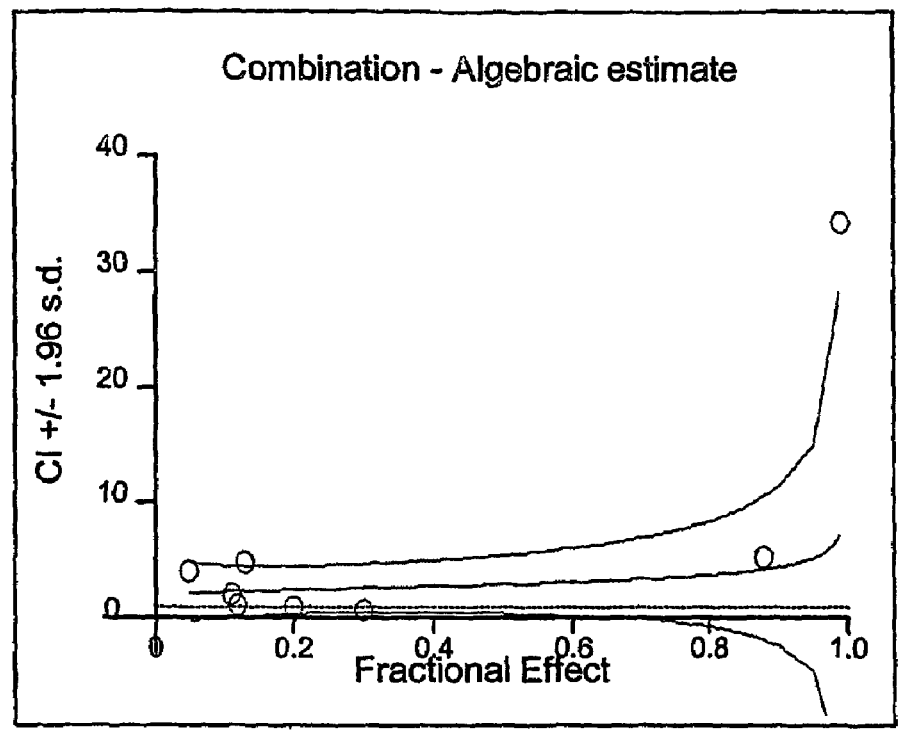
Figure 8:
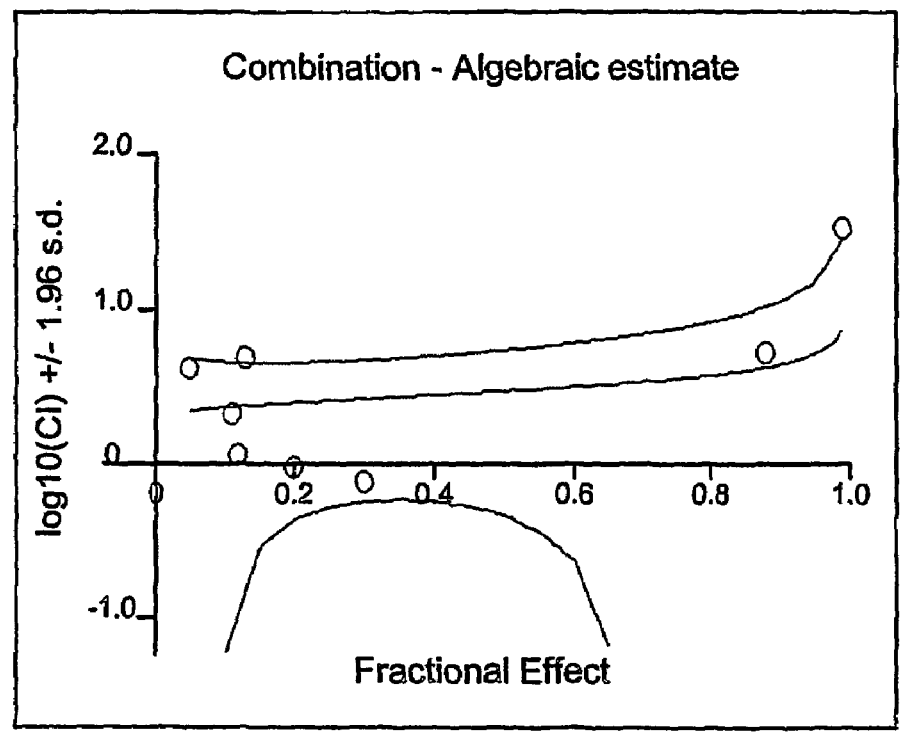

The results of Chou-Talalay analysis of combination of alidine and mthotrexate in CCRF-CEM cells can be seen in FIG. 8. The CI for this combination in CCRF-CEM cells is 0.950.

Figure 9:
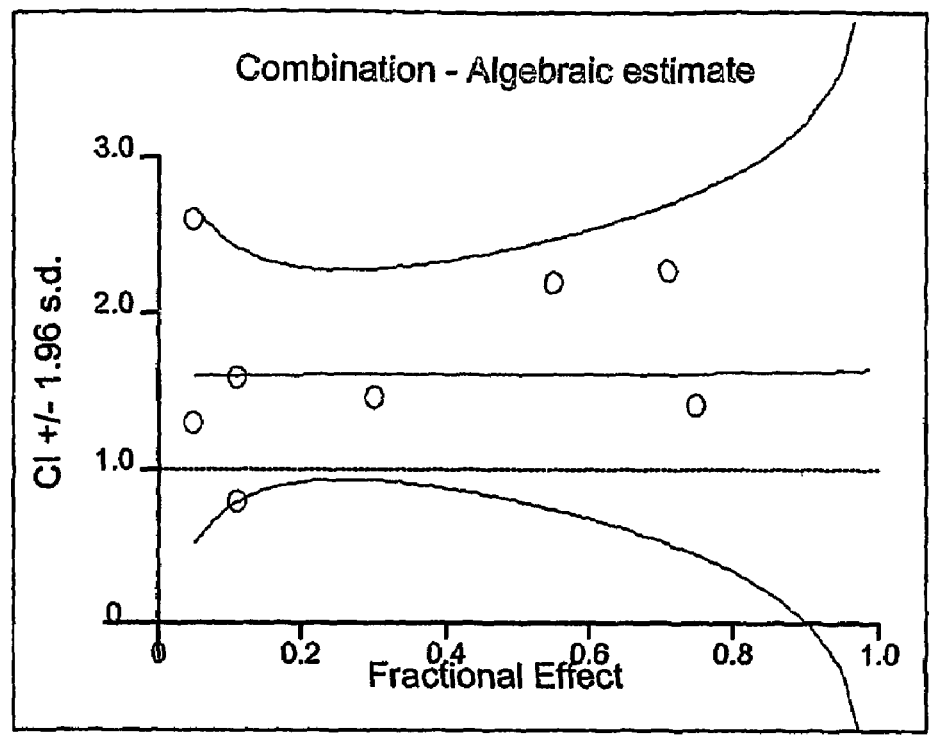
Figure 9:
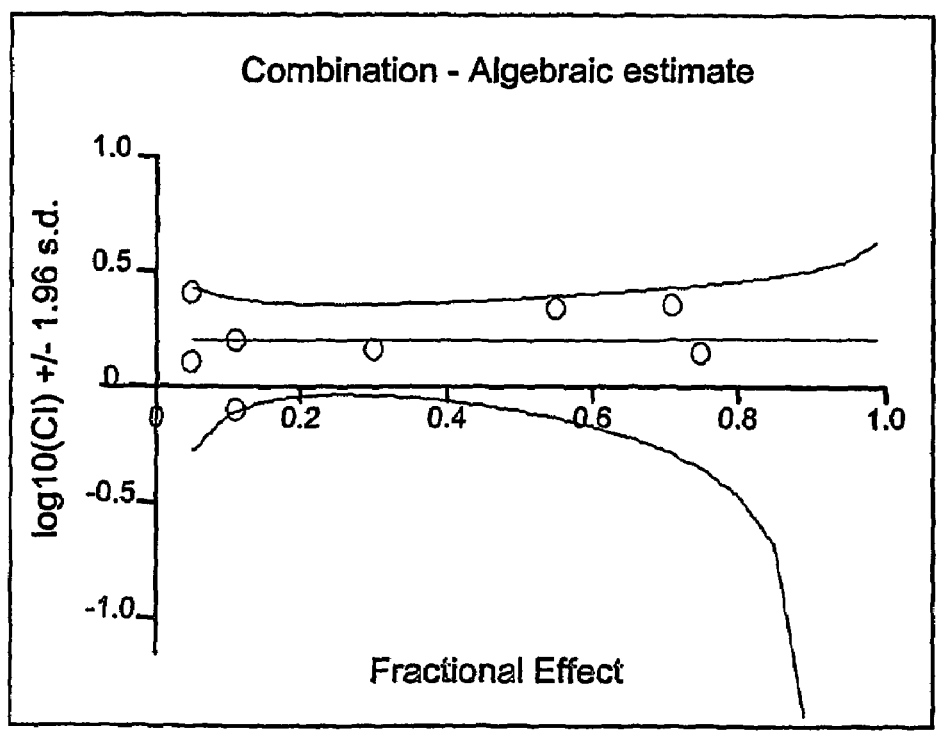

The results of Chou-Talalay analysis of combination of aplidine and Doxorubicin in CCRF-CEM cells can be seen in FIG. 9. The CI for this combination in CCRF-CEM cells is 1.952.

Figure 10:
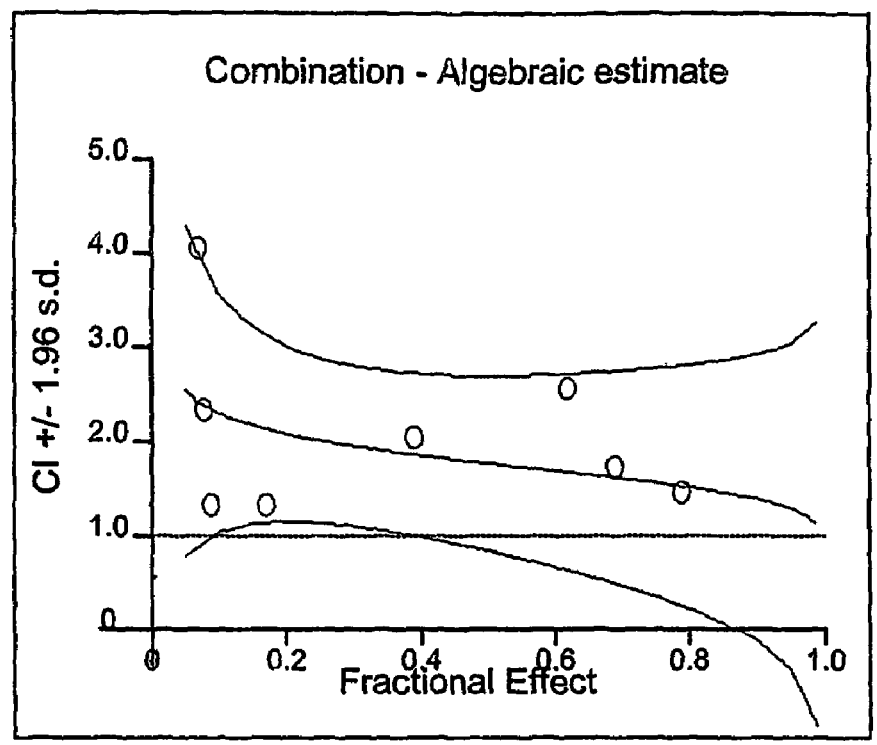
Figure 10:
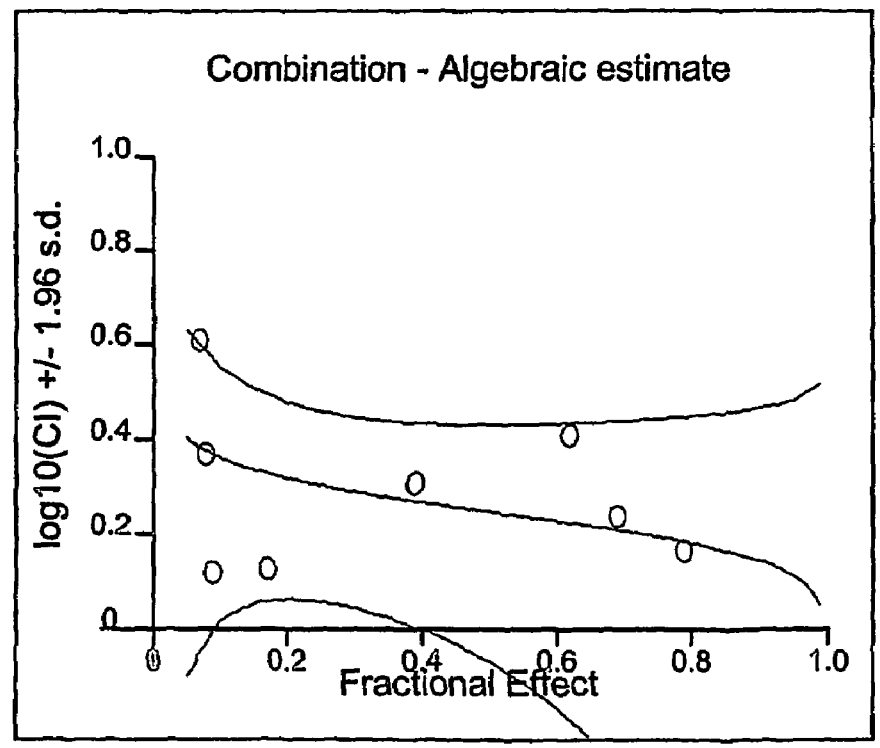

The results of Chou-Talalay analysis of combination of Aplidine and vnblastine in CCRF-CEM cells can be seen in FIG. 10. The CI for this combination in CCRF-CEM cells is 2.046.

In table 9 is shown the combination of alidine and dxorubicin with the dose of ($IC_{50}$:$IC_{50}$) in SKI-DLCL cells.

| Ratio | Dose of APL | Dose of Doxorubicin | Viability (% of control) |
|---|---|---|---|
| Control | 0 | 0 | 100 |
| IC50(APL) | 0.5 nM | 0 | 50 |
| IC50(Doxo) | 0 | 5 nM | 50 |
| ×16 | 8 nM | 80 nM | 9.4 |
| ×8 | 4 nM | 40 nM | 8.6 |
| ×4 | 2 nM | 20 nM | 8 |
| ×2 | 1 nM | 10 nM | 9.7 |
| IC50:IC50 | 0.5 nM | 5 nM | 21 |
| ×½ | 0.25 nM | 2.5 nM | 40 |
| ×¼ | 1.125 nM | 1.25 nM | 45 |
| ×⅛ | 0.0625 nM | 0.62 nM | 49 |

Figure 11:
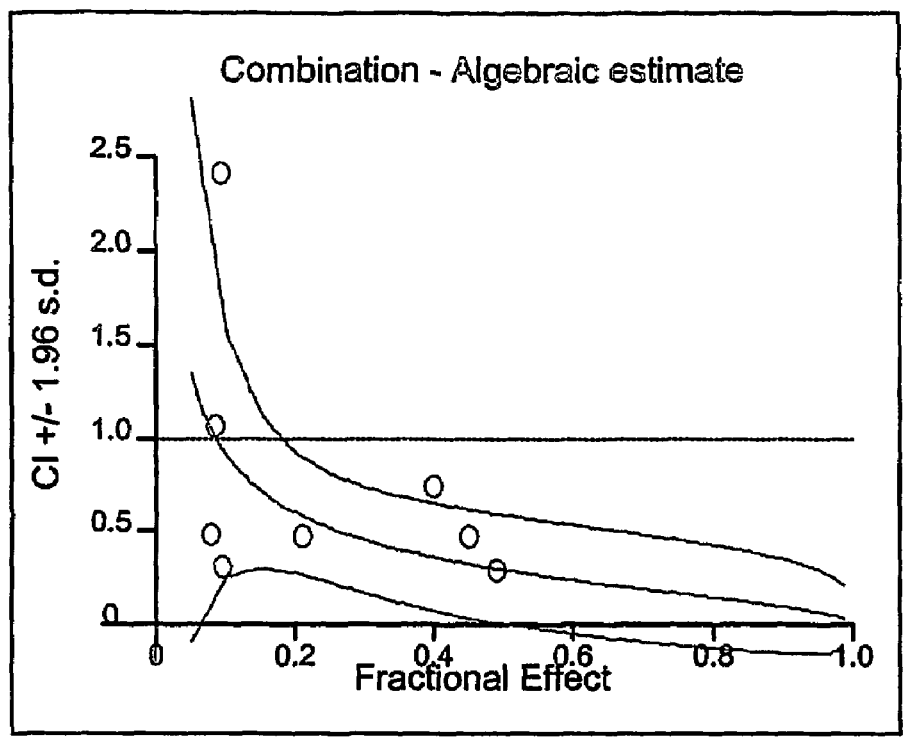
Figure 11:
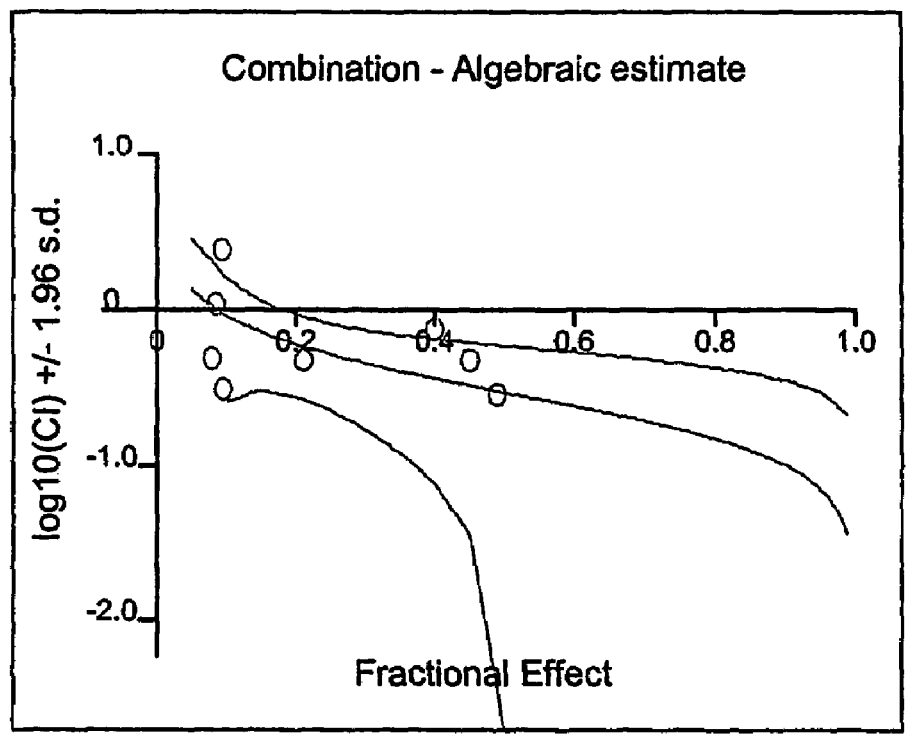

The results of Chou-Talalay analysis of combination of alidine and dxorubicin in SKI-DLCL cells can be seen in FIG. 11. The CI for this combination in SKI-DLCL cells is 0.478.

In table 10 is shown the combination of alidine and vnblastine with the dose of ($IC_{50}$:$IC_{50}$) in SKI-DLCL cells.

| Ratio | Dose of APL | Dose of Vinblastine | Viability (% of control) |
|---|---|---|---|
| Control | 0 | 0 | 100 |
| IC50(APL) | 0.5 nM | 0 | 50 |
| IC50(Vinb) | 0 | 4 nM | 50 |
| ×16 | 8 nM | 64 nM | 15 |
| ×8 | 4 nM | 32 nM | 17 |
| ×4 | 2 nM | 16 nM | 17 |
| ×2 | 1 nM | 8 nM | 21 |
| IC50:IC50 | 0.5 nM | 4 nM | 29 |
| ×½ | 0.25 nM | 2 nM | 25 |
| ×¼ | 1.125 nM | 1 nM | 28 |
| ×⅛ | 0.0625 nM | 0.5 nM | 38 |

Figure 12:
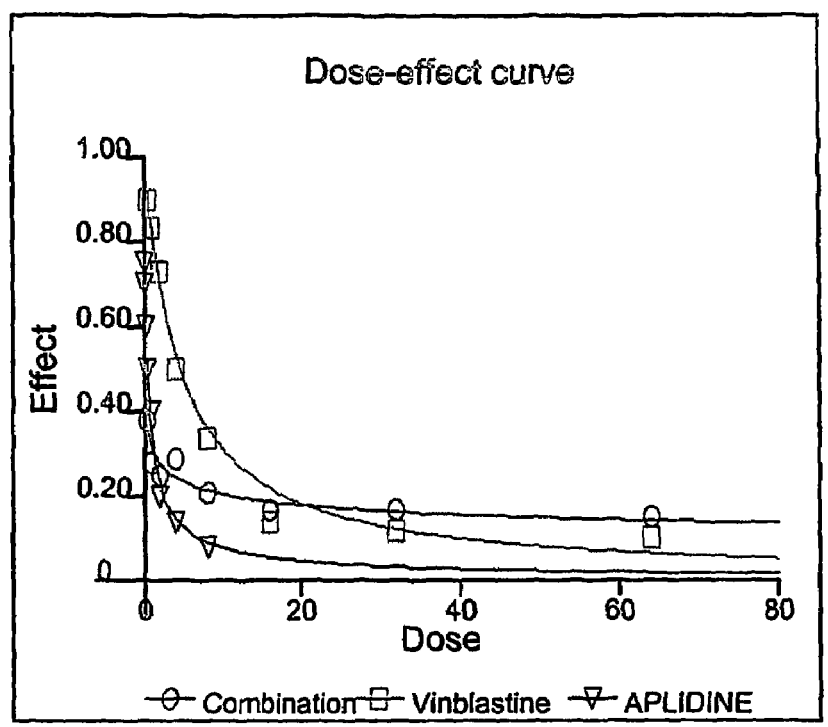
Figure 12:
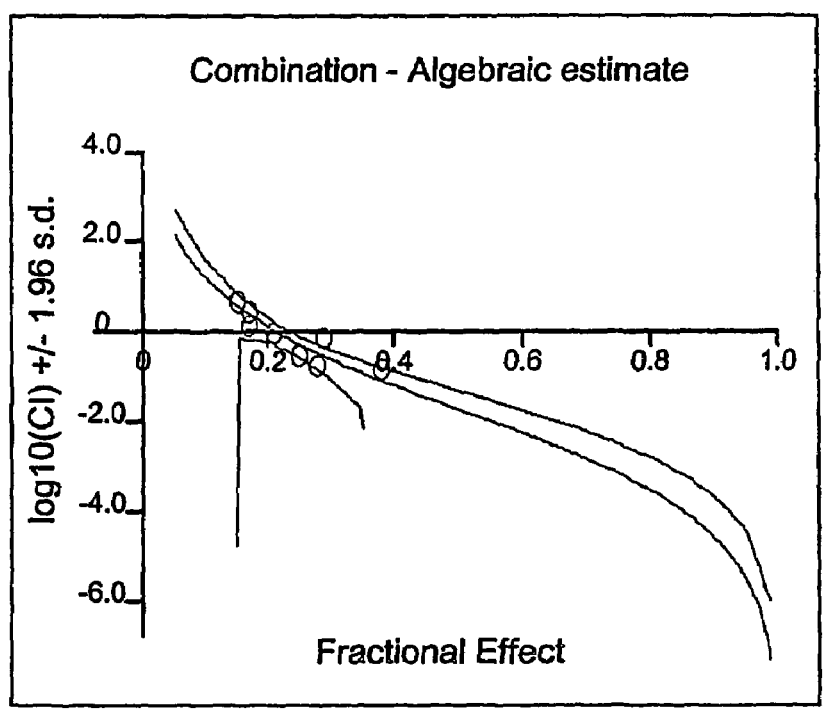

The results of Chou-Talalay analysis of combination of alidine and vnblastine in SKI-DLCL cells can be seen in FIG. 12. The CI for this combination in SKI-DLCL cells is 0.760.

In table 11 is shown the combination of alidine and mthylprednisolone with the dose of ($IC_{50}$:$IC_{50}$) in SKI-DLCL cells.

| | Dose of APL | Dose of methylprednisolone | Viability (% of control) |
|---|---|---|---|
| Control | 0 | 0 | 100 |
| IC50(APL) | 0.5 nM | 0 | 50 |
| IC50(Metpred) | 0 | 160 nM | 51 |
| ×16 | 8 nM | 2560 nM | 10.8 |
| ×8 | 4 nM | 1280 nM | 17.3 |
| ×4 | 2 nM | 640 nM | 16.7 |
| ×2 | 1 nM | 320 nM | 17.4 |
| IC50:IC50 | 0.5 nM | 160 nM | 24.7 |
| ×½ | 0.25 nM | 80 nM | 32.4 |
| ×¼ | 1.125 nM | 40 nM | 39.1 |
| ×⅛ | 0.0625 nM | 20 nM | 50 |

Figure 13:
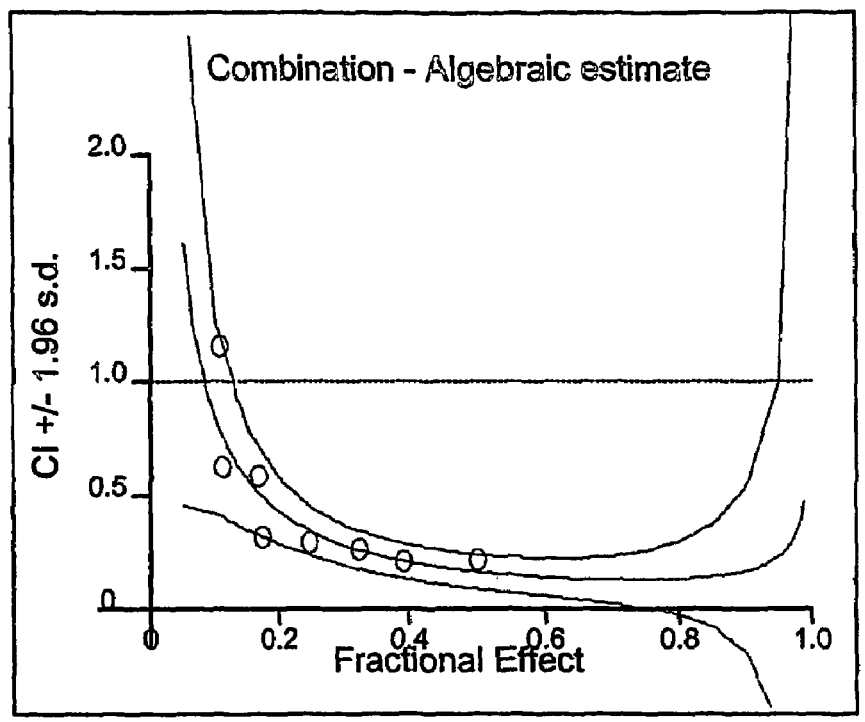
Figure 13:
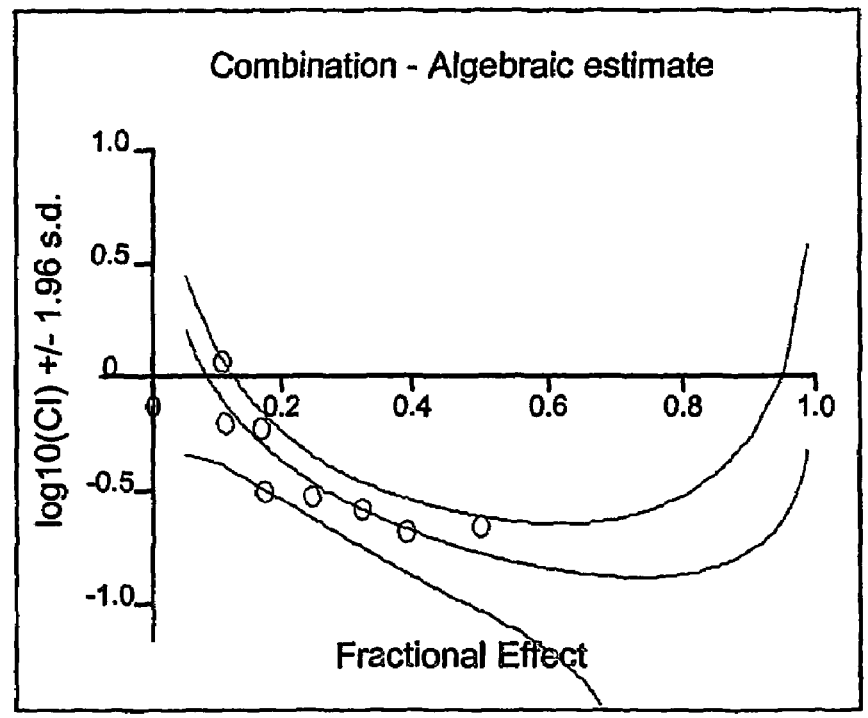

The results of Chou-Talalay analysis of combination of alidine and mthylprednisolone in SKI-DLCL cells can be seen in FIG. 13. The CI for this combination in SKI-DLCL cells is 0.646.

Example 5

We have also investigated the cytotoxic effect of combination of $IC_{20}$ (APL) with a variable dose of AraC on CCRF-CEM and SKI-DLCL cell lines. Aplidine in both cell lines potentiated the effect of AraC, the $IC_{50}$ dose of AraC was reduced from 30 nM to 1.6 nM in SKI-DLCL cell line, and from 10 nM to 0.8 nM in CCRF-CEM cell line respectively (FIG. 14). Data was obtained after cell incubation for 96 hours and using XTT asay. The results represent means of three different experiments.

Example 6

In vivo Studies

We have performed in vivo experiments to study the effect of alidine alone and in combination with other drugs for lymphoid malignancies.

Determination of Maximum Tolerated Dose (MTD) in C.B.-17 scid/scid (SCID Mice)

We have used an in vivo model of human lymphoma in SCID mice for this purpose. Specifically, we have used CCRF-CEMS cells and CB.17 scid/scid mice. We have experience with this model and have evaluated drug treatments using this xenograft (Lacerda J. F. et al. Blood 85 (10): 2675-2679 (1995)). We found that a total dose of 1 mg/kg/week given in five daily doses is the aplidine maximum dose that can be tolerated by mice.

Determination of in vivo Antitumor Effect of Alidine as a Single Agent and in Combination with AraC in SCID Mice Xenograft Model SCID mice were inoculated subcutaneously in the right flank with $10^7$ CEM-T leukemic cells. They were observed twice weekly for tumor formation at the site of inoculation. After establishment of palpable tumor, alidine was injected as single agent and in combination with several doses of AraC to determine the antitumor effect. Mice were randomized to receive alidine alone at doses of 0.75 mg/kg and 1 mg/kg, AraC alone at 50 mg/kg, or combination of Aplidine and AraC for all dose combinations. The AraC dose chosen for this combination is the dose at which the tumor growth was inhibited but no tumor regression occurred. All drugs were administered intra-peritoneally, and tumor size was compared to a control group of mice not receiving any treatment and for combination groups, compared to tumor sizes with single agent treatment.

Figure 15:
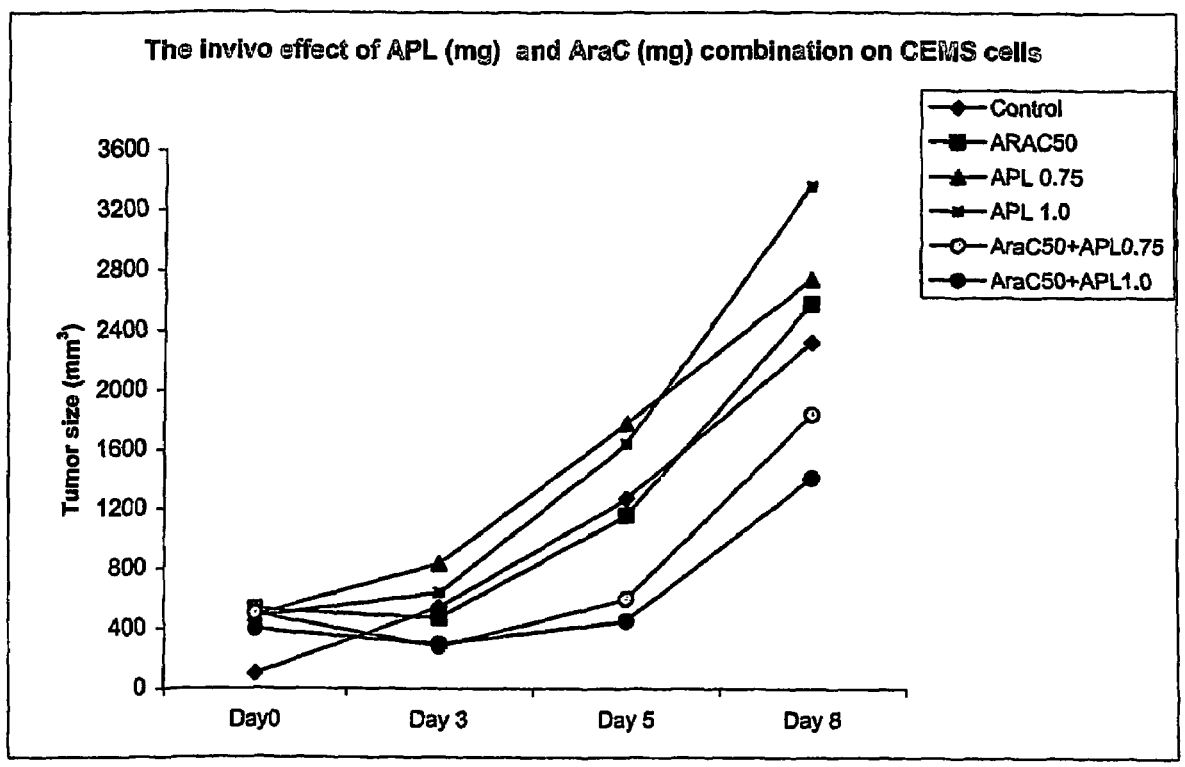

The most effective combination was found to be AraC-50 mg/kg+alidine-0.75 mg/kg (FIG. 15).

These findings in respect of aplidine can be extended to aplidine analogues, derivatives and related compounds. For example, the present invention provides a combination of a compound such as those of WO 02 02596 with an anticancer drug, preferably an anti-leukemia drug or anti-lymphoma drug, notably methotrexate, cytosine arabinoside, mitoxantrone, vinblastine, methylprednisolone or doxorubicin.

The invention claimed is:

1. A method of treating leukemia or lymphoma comprising administering to a patient in need of such treatment a synergistic amount of aplidine and a drug, wherein said drug is selected from the group consisting of methotrexate, cytosine arabinoside, mitoxantrone and methylprednisolone.

2. A method of increasing the therapeutic efficacy of a drug effective in the treatment of leukemia or lymphoma wherein said drug is selected from the group consisting of methotrexate, cytosine arabinoside, mitoxantrone and methylprednisolone, wherein said method comprises administering a synergistic amount of said drug and aplidine to a patient in need thereof.

3. The method according to claim 1 wherein said drug is methotrexate.

4. The method according to claim 1 wherein said drug is cytosine arabinoside.

5. The method according to claim 1 wherein said drug is mitoxantrone.

6. The method according to claim 1 wherein said drug is methylprednisolone.

7. The method according to claim 3 wherein said method is a method of treating leukemia.

8. The method according to claim 3 wherein said method is a method of treating lymphoma.

9. The method according to claim 5 wherein said method is a method of treating leukemia.

10. The method according to claim 5 wherein said method is a method of treating lymphoma.

11. The method according to claim 6 wherein said method is a method of treating leukemia.

12. The method according to claim 6 wherein said method is a method of treating lymphoma.

13. The method according to claim 4 wherein said method is a method of treating leukemia.

14. The method according to claim 4 wherein said method is a method of treating lymphoma.

\* \* \* \* \*

UNITED STATES PATENT AND TRADEMARK OFFICE
CERTIFICATE OF CORRECTION

PATENT NO. : 7,576,188 B2
APPLICATION NO. : 10/546750
DATED : August 18, 2009
INVENTOR(S) : Joseph R. Bertino et al.

Page 1 of 1

It is certified that error appears in the above-identified patent and that said Letters Patent is hereby corrected as shown below:

On the Title Page, please insert Item

--Related U.S. Application Data

(60) Provisional application no. 60/454,125, filed March 12, 2003--;

Column 4, line 58, please amend "arabino side" to --arabinoside--.

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,576,188 B2 |
| APPLICATION NO. | : 10/546750 |
| DATED | : August 18, 2009 |
| INVENTOR(S) | : Bertino et al. |

It is certified that error appears in the above-identified patent and that said Letters Patent is hereby corrected as shown below:

On the Title Page

Item [*] Notice:   Subject to any disclaimer, the term of this patent is extended or adjusted under 35 USC 154(b) by 299 days Delete the phrase "by 299 days" and insert -- by 338 days --

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,576,188 B2 | Page 1 of 1 |
| APPLICATION NO. | : 10/546750 | |
| DATED | : August 18, 2009 | |
| INVENTOR(S) | : Bertino et al. | |

It is certified that error appears in the above-identified patent and that said Letters Patent is hereby corrected as shown below:

On the Title page,

Item [*] Notice: Subject to any disclaimer, the term of this patent is extended or adjusted under 35 USC 154(b) by 338 days Delete the phrase "by 338 days" and insert -- by 639 days --

Signed and Sealed this

Third Day of August, 2010

David J. Kappos
*Director of the United States Patent and Trademark Office*